United States Patent [19]
Snell

[11] Patent Number: 5,749,908
[45] Date of Patent: May 12, 1998

[54] METHODS AND APPARATUS FOR ANNOTATING DATA IN AN IMPLANTABLE DEVICE PROGRAMMER USING DIGITALLY RECORDED SOUND

[75] Inventor: Jeffery D. Snell, Oak Park, Calif.

[73] Assignee: Pacesetter, Inc., Sylmar, Calif.

[21] Appl. No.: 768,734

[22] Filed: Dec. 18, 1996

[51] Int. Cl.[6] .................................................. A61N 1/36
[52] U.S. Cl. ........................................................ 607/30
[58] Field of Search .............................. 607/30, 31, 32, 607/60

[56] References Cited

PUBLICATIONS

United States Statutory Invention Registration H1347, Greeninger et al, Aug. 1994.

*Primary Examiner*—Scott Getzow

[57] ABSTRACT

Methods and apparatus are provided for annotating medical data in an implantable device programmer using digitally recorded sound. A display screen of the implantable device programmer preferably displays at least a portion of a patient data set. A user preferably designates a connection point of the patient data set. Voice signals from the user are received by a transducer and converted to electrical signals, which are then converted to digital data by an analog to digital converter. The digital voice data preferably are stored within a memory device of the implantable device programmer and preferably are linked to the connection point. A marker preferably is displayed on the display screen at a location corresponding to the connection point. The physician is able to listen to the voice annotation by selecting a playback button displayed on the display screen. Voice annotations preferably can be transcribed into text which preferably is displayed in a text window when the voice annotation marker is selected.

32 Claims, 22 Drawing Sheets

| I.D. | TIME | TRANSCRIBED |
|---|---|---|
| A ⌐412 | ⌐7/10/96 (2:09 pm) | N ⌐416 |
| C | 7/10/96 (2:40 pm) | N |
| D | 7/10/96 (3:06 pm) | N |
| F | 7/21/96 (11:20 am) | Y |

410 — 414 — 406

[TRANSCRIBE] 418    [DONE] 442

```
436
One AIEGM pulse had an unusually high voltage
differential of about 1.5 millivolts.
(Dr. Stevens)

SELECTED:    A        7/10/96 (2:09 pm)              [SAVE]
```
408

420   422   424   438

[PLAY] 426   [STOP] 428   [F F] 430   [REWIND] 432

[RESTART] 434                         [DELETE] 440

*Fig. 18*

| I.D. | TIME | TRANSCRIBED |
|---|---|---|
| A | 7/10/96 (2:09 pm) | N |
| C | 7/10/96 (2:40 pm) | N |
| D | 7/10/96 (3:06 pm) | N |
| F | 7/21/96 (11:20 am) | Y |

[TRANSCRIBE] [DONE]

> One AIEGM pulse had an unusually high voltage differential of about 1.5 millivolts. (Dr. Stevens)

SELECTED: A 7/10/96 (2:09 pm) [SAVE]

[PLAY] [STOP] [FF] [REWIND]
[RESTART] [DELETE]

FIG. 21

METHODS AND APPARATUS FOR ANNOTATING DATA IN AN IMPLANTABLE DEVICE PROGRAMMER USING DIGITALLY RECORDED SOUND

BACKGROUND OF THE INVENTION

This invention relates to implantable medical devices and particularly to implantable cardiac stimulating devices, including implantable cardiac pacemakers and implantable cardiac defibrillators, as well as implantable cardioverters and cardioverter/defibrillators. More particularly, this invention relates to an analyzer-programmer computer for monitoring and altering the performance of such implantable medical devices, which allows a user to record voice annotations.

Implantable medical devices are used to treat a variety of conditions. Implantable cardiac stimulating devices, such as pacemakers and cardioverter-defibrillators, are examples of implantable medical devices which are used to provide therapy for various pathological cardiac arrhythmias.

Most modern implantable cardiac stimulating devices sense electrical signals produced by the heart and then apply electrical stimulation to the heart based on the detected signals. With every beat of the patient's heart, the implantable cardiac stimulating device makes decisions as to whether electrical stimulation is necessary and what type of electrical stimulation to apply. These decisions involve the analysis of medical data gathered in real-time and the comparison of the gathered medical data against standards by a computer program executed by a processor within the implantable cardiac stimulating device.

The computer program carries out orders given by the patient's physician. These orders are tailored by the physician for a particular patient based upon the physician's training and experience. Thus, the computer program is not an unalterable set of instructions burned into the implantable cardiac stimulating device at the time of manufacture. Note the term physician is used in this application to include veterinarian and the term patient includes both humans and animal patients.

Typically, a specialized computer called an analyzer-programmer is used to communicate telemetrically with the implantable cardiac stimulating device. The analyzer-programmer allows the physician to analyze the patient's situation and reset the programming parameters of the implantable cardiac stimulating device, or allows another medical specialist to do so at the request of the physician. The physician may use the analyzer-programmer to customize the programming parameters as part of the procedure to implant the implantable cardiac stimulating device. After the device is implanted, the physician typically monitors the performance of the patient's heart, the implantable cardiac device's recognition and characterization of the patient's sinus rhythm, the implantable cardiac stimulating device's choice and timing of therapeutic electrical stimulation, and the reaction of the patient's heart to the therapy.

To accomplish such programming and monitoring, the implantable cardiac stimulating device is capable of receiving and transmitting information from its implanted location to a telemetry head placed on or near the surface of the patient's body. The process of evaluating the performance of the implanted cardiac stimulating device typically involves the analysis of atrial intercardiac electrograms (AIEGMs) and ventricular intercardiac electrograms (VIEGMs) telemetered out to the analyzer-programmer from the implantable cardiac stimulating device. The AIEGM and VIEGM are sources of information for use by the implantable cardiac stimulating device in monitoring the heart. The implantable cardiac stimulating device may also transmit marker data to the analyzer-programmer. The marker data allow the physician to identify occurrences of sensed or paced cardiac events.

A physician or medical specialist typically records an evaluation of the patient's condition or diagnosis, and may also record instructions for medical personnel as to the disposition of the patient's records. For example, a physician may record the progress made by the patient since the last visit, the success of a particular therapy, and the patient's status report distribution list (i.e., additional persons who should receive information about the patient's current status).

This type of information is usually recorded by the physician using a conventional audio tape recorder, or by making written notes. However, using an audio tape (or written notes) to record and store patient information has certain disadvantages. For example, the tape (or written notes) may be misplaced or mixed up with other tapes (or written notes). Typically, the tape (or written notes) are given along with the patient's other data to appropriate medical personnel who listen to and act on the recorded instructions. The tape (or written notes) may be misplaced or mixed up with other tapes (or written notes) during this process. In addition, since multiple messages are often recorded on a single audio tape, finding a particular piece of information on the tape can be tedious and time consuming because one must locate the position on the tape where the desired information resides.

U.S. patent application Ser. No. 08/510,367, filed Aug. 2, 1995, of Snell and Levin, entitled "Improved User Interface for an Implantable Medical Device Using an Integrated Digitizer Display Screen" ("the '367 application"), which is hereby incorporated by reference, describes a user interface which, among numerous other functions, permits a user to annotate data with digitized, handwritten notes. This system greatly reduces the possibility of the information being lost or mixed up with other records because the digitized annotations are stored in a computer memory device along with the associated patient data. However, inputting the information using a digitizer pen can be more time consuming than using a tape recorder. In particular, it may be impractical to input a large amount of information, such as a relatively lengthy summary of a patient's condition, using a digitizer pen.

In view of the foregoing, it would be desirable to provide an easy-to-use, convenient, and secure manner for a physician to record an evaluation of a patient.

In particular, it would be desirable to allow a physician to record spoken statements and then store those recorded statements as digital data within the analyzer-programmer. Such a system would allow the physician to securely record patient information, including lengthy summaries of the patient's condition.

A system for controlling an implantable device programmer using voice commands is described in U.S. patent application Ser. No. 08/664,070, filed Jun. 13, 1996 of Snell, entitled "Methods and Apparatus for Controlling an Implantable Device Programmer Using Voice Commands" ("the '070 application"). This system recognizes voice commands given by a user and uses the commands to control an implantable device via a telemetry circuit. However, the '070 application does not allow a user to record digital voice data associated with patient data displayed on the display screen of the implantable device programmer.

SUMMARY OF THE INVENTION

The present invention provides methods and apparatus for allowing a user to record voice annotations. In a preferred embodiment, an implantable device programmer is provided which includes a processing circuit, a memory device coupled to the processing circuit for storing digital data, a display screen coupled to the processing circuit for displaying a graphical representation of at least a portion of a patient data set, a transducer for converting audio signals into electrical signals, and an analog to digital converter coupled to the processing circuit and the transducer for converting the electrical signals into digital voice data. The digital voice data are stored in the memory device and are linked to a portion of the patient data set.

The implantable device programmer preferably has an input device coupled to the processor circuit for designating the portion of the patient data set to which the digital voice data are to be linked. A digitizer pen, for example, can be used as the input device. The input device preferably is used by a user (such as a physician or medical specialist) to designate the portion of the patient data set to which the digital voice data are to be linked.

In a particularly preferred embodiment, the user links the digital voice data to the patient data set by designating a connection point using the input device. A voice annotation marker preferably is displayed on the display screen at a location corresponding to the connection point.

The implantable device programmer preferably has at least one speaker coupled to the processor circuit for playing back the digital voice data. The digital voice data preferably are played back via the speaker when a playback indicator displayed on the display screen is selected using the input device.

The implantable device programmer preferably has a conventional keyboard coupled to the processor circuit for transcribing the digital voice data. The transcribed digital voice data preferably are linked to the portion of the patient data set to which the digital voice data are linked. A voice annotation marker which indicates that the voice annotation has been transcribed preferably is displayed on the display screen at a location corresponding to the portion of the patient data to which the digital voice data are linked. The transcribed digital voice data preferably are displayed on the display screen when the voice annotation marker is selected using the input device.

In an alternative embodiment, a digitizer pen is used to transcribe the digital voice data by writing on a digitizer display screen so as to provide transcribed digital voice data which are stored in the memory device.

The present invention also provides methods for operating an implantable device programmer. In a preferred embodiment, the method is used with an implantable device programmer having a processing circuit, a memory device coupled to the processing circuit, a display screen coupled to the processing circuit, a transducer, and an analog to digital converter coupled to the processing circuit and the transducer. In accordance with a preferred embodiment of a method of the present invention, a graphical representation of at least a part of a patient data set is displayed on the display screen. Audio signals are received and converted into electrical signals by the transducer. The electrical signals are then converted into digital voice data by the analog to digital converter. The digital voice data are stored in the memory device, and are linked to a portion of the patient data set.

The implantable device programmer preferably has an input device coupled to the processor circuit, and the step of linking the digital voice data to a portion of the patient data set preferably comprises designating the portion of the patient data set to which the digital voice data are to be linked using the input device.

A voice annotation marker preferably is displayed on the display screen at a location corresponding to the portion of the patient data set to which the digital voice data are linked.

The implantable device programmer preferably has at least one speaker, and the method preferably includes the step of playing back the digital voice data using the speaker. The digital voice data preferably are played back when a playback indicator displayed on the display screen is selected using the input device.

The implantable device programmer preferably has a conventional keyboard coupled to the processing circuit, and the method preferably includes the steps of transcribing the digital voice data using the keyboard so as to provide transcribed digital voice data, and storing the transcribed digital voice data in the memory device. A voice annotation marker preferably is displayed on the display screen at a location corresponding to the portion of the patient to which the digital voice data are linked.

The transcribed digital voice data preferably are displayed on the display screen when the voice annotation marker is selected using the input device.

In a alternative embodiment, the input device is a digitizer pen and the display screen is a digitizer display screen, and the method includes the steps of transcribing the digital voice data by writing on the digitizer display screen with the digitizer pen so as to provide transcribed digital voice data, and storing the transcribed digital voice data in the memory device.

The apparatus and methods for recording voice annotations provided by the present invention can be used to record any type of information, including, but not limited to, an evaluation of the patient's condition or diagnosis, and instructions for medical personal as to the disposition of the patient's records. Recording a voice annotation in accordance with the present invention allows the physician to easily, conveniently, and securely record such information.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 18 is a preferred screen display after a voice annotation has been transcribed;

FIG. 21 is an alternative screen display showing a voice annotation that has been transcribed using a digitizer pen;

DETAIL DESCRIPTION OF THE PREFERRED EMBODIMENTS

For purposes of illustration, the present invention is described hereinbelow in the context of the portable, pen-based analyzer-programmer described in the above-incorporated '367 application. Those skilled in the art will appreciate, however, that the present invention is not limited to use with a pen based analyzer-programmer, but has much broader applications. In alternative embodiments, the present invention can be implemented in conventional, non-portable analyzer-programers having conventional keyboard input devices, as well as analyzer-programmers having touch screen input devices.

Figure 1:
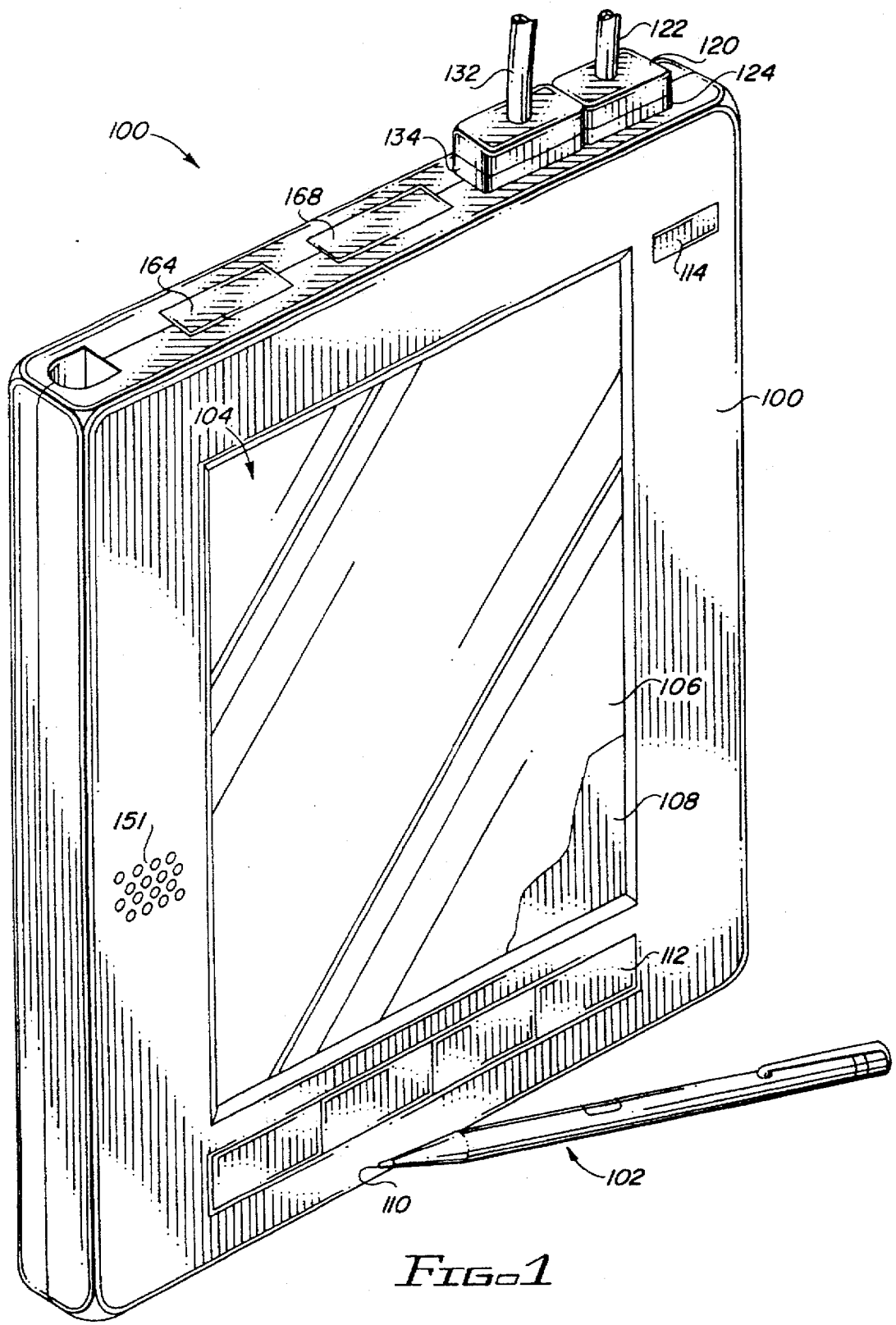
FIG. 1 is a perspective view of a preferred tablet computer for use with the present invention.

Referring to FIG. 1, a tablet computer 100, and a pen 102 for inputting information are shown along with components of the tablet computer. The pen 102 can be used to write, draw, or select among presented choices. The pen 102 is effective on a digitizer display screen 104. The digitizer display screen 104 comprises the majority of the front face of the tablet computer 100. The digitizer display screen 104 is comprised of a display 106 and a digitizer 108 which overlap one another. The digitizer 108 preferably is underneath the display 106. The term "underneath" and the phrase "on the surface over" shall be used to describe the corresponding positions of the digitizer 108 and the display 106, respectively. The terms "above" and "below" will be used to describe position in the plane of the display 106 or the digitizer 108.

The pen 102 preferably is one of the commercially available pens that alter a radio frequency signal transmitted by the digitizer 108. This altered signal is sensed by the digitizer 108 when the pen 102 is within the sensing range of the digitizer 108. The sensing range is approximately one-quarter inch. Contact of a pen tip 110 with any surface causes a very slight movement of the pen tip 110 back into the body of the pen 102. This depression of the pen tip 110 triggers a switch (not shown) within the pen 102 and changes the way the pen 102 alters the transmitted signal. Typically, the depressed tip signal is used for input and the other pen signal is used as a feedback signal to help the physician or medical specialist place the pen 102. The tablet computer 100 responds to the pen input by causing an image to be displayed on the display 106.

Emergency keys 112 preferably are provided on the tablet computer 100. The emergency keys 112 provide the physician or medical specialist with several important functions for controlling the tablet computer 100 during an emergency. One of the emergency keys 112 may request that the tablet computer 100 send a particular command to the implantable medical device (described below in connection with FIG. 2), or may request action by the tablet computer 100 itself such as a reset of the tablet computer 100 or a request of the tablet computer 100 to display a screen display with information and options that are useful when managing an emergency. The emergency keys 112 allow the physician or medical specialist to intervene quickly even if the pen 102 is misplaced. The emergency keys 112 allow action without the delay inherent in entering the sequence of commands that would otherwise be required to request the tablet computer 100 to display the screen display with the emergency functions.

The tablet computer 100 is powered by a battery (described below in connection with FIG. 2). The tablet computer 100 is turned on and off with an on/off switch 114.

Figure 2:
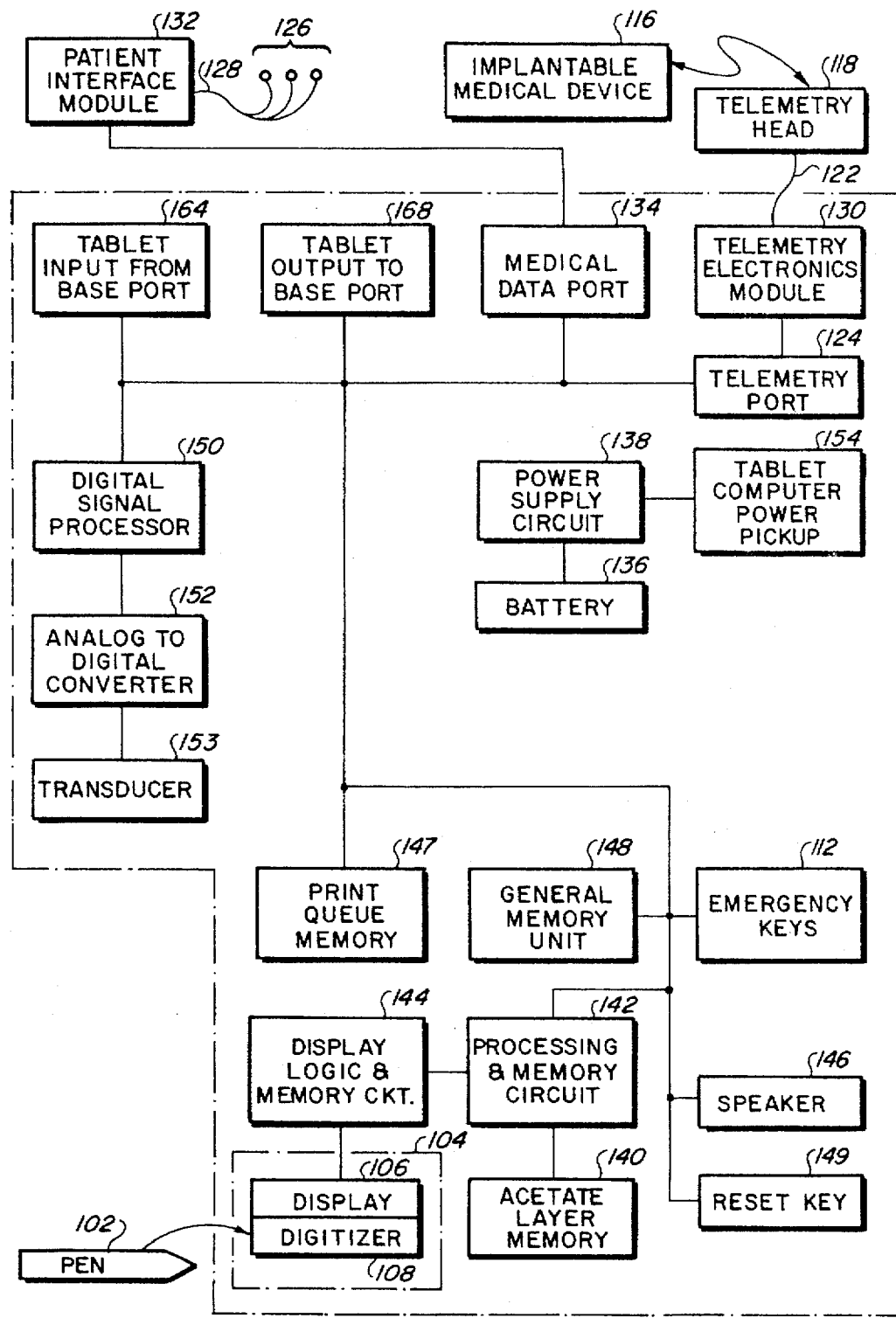
FIG. 2 is a block diagram of the tablet computer of FIG. 1 showing functional elements.

Referring now to FIG. 2, an implantable medical device 116 can sense cardiac activity and provide therapeutic electric stimulation through electrical leads (not shown). The information received by the implantable medical device 116 include IEGM waveforms from the atrial and ventricular regions of the heart, and marker data channel information generated within the implantable medical device 116. Marker data channel information contains a record of discrete acts of the implantable medical device 116 such as the application of a therapeutic electric pulse, and also the recognition by the implantable medical device 116 of certain heart activities as sensed by the implantable medical device 116.

The AIEGM measurement information, VIEGM measurement information, marker data channel information, and the time of each measurement and each marker data channel marker can be stored in a limited amount of memory (not shown) within the implantable medical device 116. The current (real-time) or stored medical data in the implantable medical device can be transmitted through the tissue and skin of the patient to a telemetry head 118.

The term "real-time" does not necessarily mean instantaneous. The term is in contrast with "batch processed" information. "Real-time" refers to a system that controls an ongoing process and delivers the output not later than the time that it is needed for effective control. Thus, the cardiac data is real-time data (or current data) even if the various processing steps introduce a delay between a cardiac event and the display of the cardiac information.

The telemetry head 118 is attached to a telemetry electronics module 120 by a telemetry cable 122 which is preferably approximately six feet long. The telemetry electronics module 120 is plugged into a telemetry port 124. (Note that the connection of the telemetry cable 122 into the telemetry electronics module 120 and the telemetry port 124 is also shown in FIG. 1.) The telemetry electronics module 120 performs conversions of the telemetry data such as a conversion from analog data to digital data if the implantable medical device 116 does not itself perform the analog-to-digital conversion. The preferred embodiment uses the same cable and port for telemetry data transmitted in either direction between the tablet computer 100 and the implantable medical device 116. A system (not shown) with an output port on the tablet computer 100 and a cable dedicated to output along one communication path to the telemetry head 118 and having a separate input port on the tablet computer 100 with a separate cable dedicated to input from a separate communication path to the telemetry head 118 could also use the teachings of this invention.

Another channel of medical data can be collected from surface ECG leads 126. The surface ECG leads 126 are placed on the skin of the patient (not shown). A surface ECG cable 128 has a number of strands that preferably can be attached and detached to the surface ECG leads 126. The surface ECG leads 126 are connected via the surface ECG cable 128 to a patient interface module 130 which performs conversion of the surface ECG waveform into digital format and performs other processing of the waveform data. The patient interface module 130 is connected to the tablet computer 100 by a medical data port cable 132 at a medical data port 134. (Note that the connection of the medical data port cable 132 to the medical data port 134 is also shown in FIG. 1.)

The tablet computer 100 is provided with energy during mobile operation by a battery 136 connected to a power supply circuit 138. The digitizer display screen 104 is shown in FIG. 2 in its constituent parts: the digitizer 108 and the display 106. The input from the pen 102 is received by the digitizer 108 and placed in an acetate layer memory 140 where the input is processed in processing and memory circuit 142.

The term acetate layer memory is used to describe a section of memory that stores information that is displayed as an overlay over some other information. Acetate layer memory is so called because the overlay information seems to be stored on a transparent layer of acetate and that can be selectively overlaid over the other information. Thus, the term is descriptive of the function of the memory rather than the type of memory. The processing and memory circuit 142 interprets the input, and then deletes the input from the acetate layer memory 140 and moves a copy of certain input into a display logic and memory circuit 144. The display logic and memory circuit 144 controls the display 106.

In accordance with the present invention, a speaker 146 preferably is used to play back digital voice data recorded by the tablet computer 100. The speaker 146 preferably is also used to provide audio alarms in response to detected problems concerning the patient's heart, the monitoring equipment, the input from the physician or medical specialist, or other problems. The speaker 146 can also be used to confirm receipt of input.

The tablet computer 100 contains a print queue memory 147 which stores requests to create printouts until the tablet computer 100 is connected directly or indirectly to a printer (described below in connection with FIG. 3). The print queue memory 147 is non-volatile memory and preferably is a memory card.

In addition to the acetate layer memory 140, the memory in the processing and memory circuit 142, the memory in the display logic and memory circuit 144, and the non-volatile memory in the print queue memory 147, the tablet computer 100 has a general memory unit 148. The general memory unit 148 preferably is used to store patient data and reference material available to the physician or medical specialist such as a dictionary, phone directory, medical reference text, or reference manuals on implantable medical controllers A conventional hard drive preferably is used for the general memory unit 148. Alternative choices for the general memory unit include a non-volatile memory card or a read and write optical memory. Another alternative (not shown) is to use a read only memory device to store the reference material. This read only memory would be on a cartridge, optical disk or other easily replaced device so that periodic updates could be made to the reference material.

In addition to the emergency keys 112, a reset key 149 is preferably provided to re-initialize the tablet computer 100. Alternatively, the reset key could be one of the emergency keys 112.

In accordance with the present invention, a transducer 150 is provided in order to receive voice data from the physician. The transducer 150 preferably is mounted under perforations 151 (FIG. 1) in the tablet computer 100. (In an alternative embodiment (not shown), a separate transducer which plugs into a tablet computer is provided.) The transducer 150 preferably converts audio signals to analog electrical signals. An analog to digital (A/D) converter 152 preferably converts the analog electrical signals into digital data. The digital data from the A/D converter 152 preferably are preprocessed by a digital signal processor (DSP) 153 before passing to the processing and memory circuit 142. (In an alternative embodiment (not shown) the DSP is omitted and the digital data from the A/D converter preferably pass directly to the processing and memory circuit.)

Figure 3:
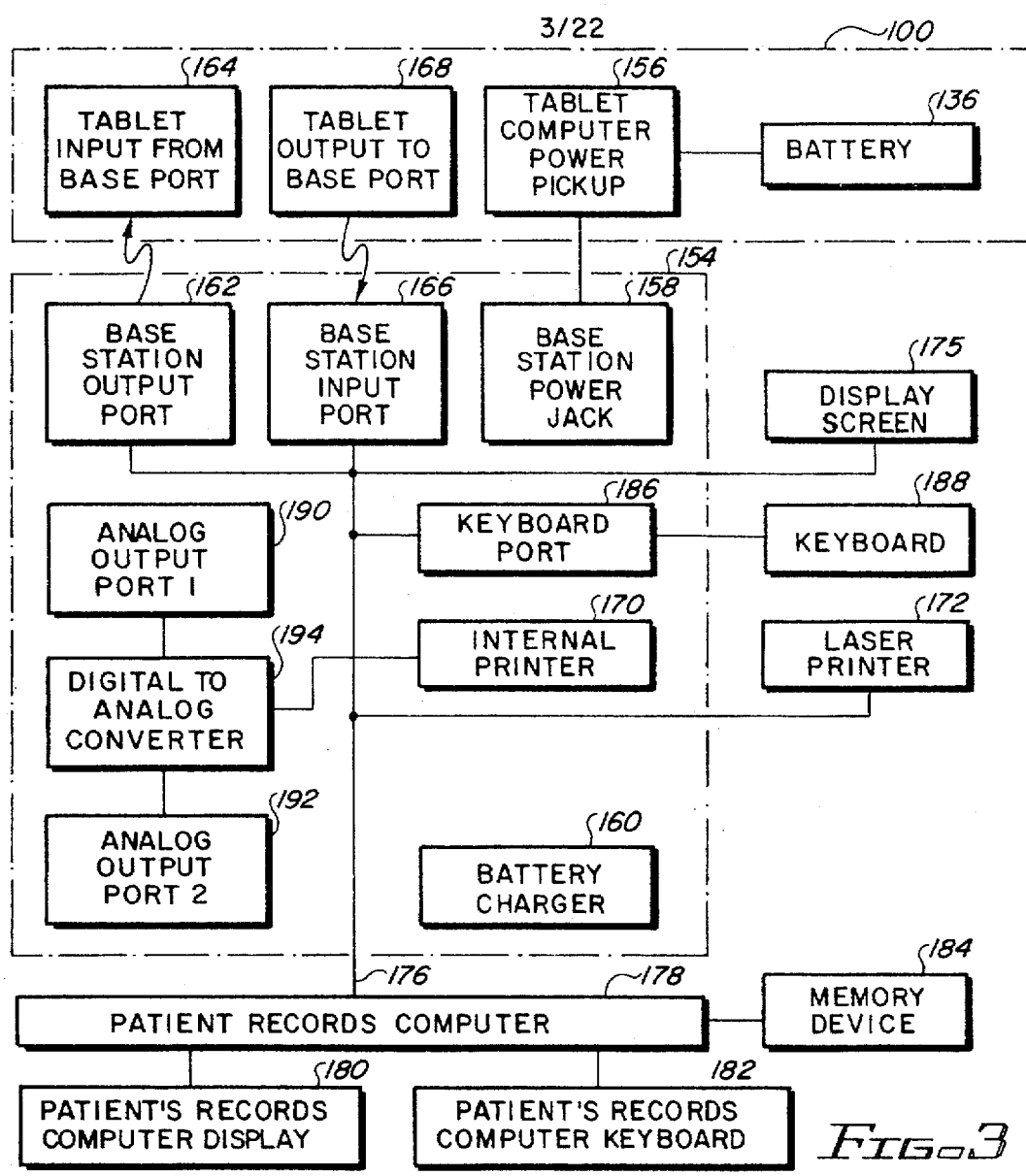
FIG. 3 is a block diagram of the tablet computer of FIGS. 1 and 2, showing the tablet computer connected to a base station, the base station being further connected to a patient records computer and to peripheral devices.

Referring now to FIG. 3, the tablet computer 100 is periodically inserted into a base station 154. A tablet computer power pickup 156 mates with a base station power jack 158 during the insertion of the tablet computer 100 into the base station 154 to provide a source of power to the tablet computer 100 which is sufficient to both operate the tablet computer 100 and to charge the battery 136 in the tablet computer 100. A battery charger 160 is contained in the base station 154 for charging batteries 136 for use in the tablet computer 100. The base station 154 is equipped with conventional power supply circuitry (not shown) connected to line voltage by a line voltage plug (not shown).

The base station 154 and tablet computer 100 have connections that allow the tablet computer 100 to communicate with the base station 154 when inserted in the base station 154. LEDs (light emitting diodes) preferably are used for an infrared serial communication link between the tablet computer 100 and the base station 154. Specifically, a base station output port 162 preferably is placed adjacent to a tablet input from base port 164 and a base station input port 166 preferably is placed adjacent to a tablet output to base port 168. These ports preferably are small windows for transmitting the infrared signals. As shown in FIG. 3, small gaps exists between the communication ports (162 to 164 and 166 to 168) as distinguished from the physical contact established between the base station power jack 158 and the tablet computer power pickup 156.

Although conventional physical cable connections could be used, the infrared serial connection is preferred over conventional physical cable connections for two reasons. The first reason is that the infrared connections are not subject to physical wear and tear from the repeated insertion and removal of the tablet computer 100 into the base station 154.

The second reason to use infrared connections instead of conventional physical connections is electrical isolation of the tablet computer 100 from other equipment. Electrical isolation is important in the design of medical equipment because of concerns for patient safety.

An internal printer 170 preferably is integral to the base station 154. The internal printer 170 is preferably a thermal printer. A laser printer 172 preferably is connected to the base station 154 by a laser printer connection cable 174. Other printers (not shown) such as ink jet printers or dot matrix printers with resolutions sufficient to reproduce the medical data may also be used. A display screen 175 preferably is connected to the base station 154.

The base station 154 is at least periodically connected by a base to host cable 176 to a patients' records computer 178. The patients' records computer 178 is connected to a patients' records computer display 180, a patients' records computer keyboard 182, and a memory device 184. The memory device 184 stores medical data records and other information that is relevant to the use of the tablet computer 100.

The base station 154 preferably has a keyboard port 186 for connecting a keyboard 188. The keyboard 188 preferably can be used by field service engineers in customizing the tablet computer 100, and preferably can be used to transcribe voice annotations (as described below in connection with FIGS. 17-18). An optional attachment is a bar code reader (not shown) which could be connected to the keyboard port 186 to allow bar codes to be scanned. As an example of bar code reader use, some hospitals may position the base station 154 along with the bar code reader into the operating room to read a patient identification bar code number along with the bar code representation of each piece of equipment or material used during the implantation of the implantable medical device 116 (FIG. 2).

Analog output ports 190 and 192 are provided so that other devices can be connected to the base station 154. The medical data provided to the tablet computer 100 through the medical data port 134 (FIG. 2) and the telemetry port 124 (FIG. 2) can be passed through the tablet output to base port 168 to the base station input port 166 and converted into analog form in a digital-to-analog converter 194 before passing out of one of the analog output ports 190 or 192 to peripheral devices such as paper chart recorders (not shown), large video monitors (not shown) for use in teaching, or calibration equipment (not shown).

Figure 4:
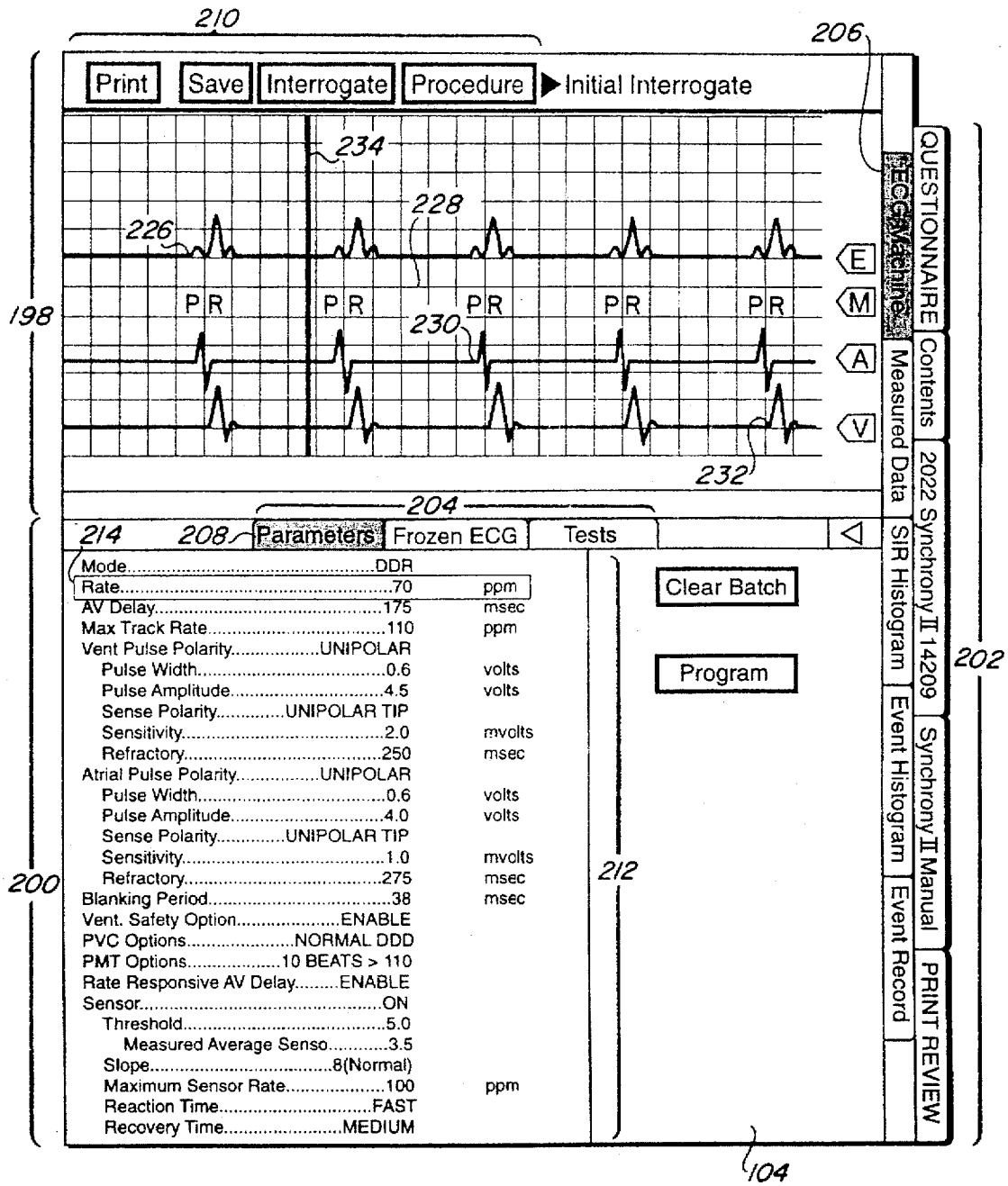
FIG. 4 is a sample screen display on the digitizer display screen of the tablet computer.

A view of the digitizer display screen 104 is shown in FIG. 4. The screen display has an upper window 198 and a lower window 200. The screen display contains vertical tabs 202 and horizontal tabs 204. The physician or medical specialist uses the vertical and horizontal tabs 202 and 204 to move from one screen display to another screen display. Tapping one of the vertical tabs 202 triggers the button on the digitizer display screen 104 underneath the displayed image of the tab. This tapping will cause the tablet computer 100 (FIG. 1) to jump to the first screen display in a series of related screen displays. Vertical tabs 202 are preferably made to resemble tabs on a three-ring binder in order to facilitate intuitive use.

Individual windows may have horizontal tabs 204. In FIG. 4, the lower window 200 has horizontal tabs 204 to change the lower window 200 without affecting the rest of the screen display. A highlighted vertical tab 206 and a highlighted horizontal tab 208 remind the physician or medical specialist of the context of the current screen display. In this case, the highlighted vertical tab 206 displays the tab labeled "ECG Machine" and the highlighted horizontal tab 208 displays the tab labeled "Parameters."

In this screen display, a series of buttons 210 are above the upper window 198 on the digitizer display screen 104. The series of buttons 210 contain choices such as print or save that are used in a large number of screen displays. The button choices are updated by the tablet computer 100 (FIG. 1) to reflect currently valid choices. A series of programming parameters 212 is displayed in the lower window 200. A rectangle 214 preferably is displayed as a visual aid for the physician or medical specialist. The rectangle 214 appears when the pen 102 (FIG. 1) is within sensing range of the digitizer display screen 104. The rectangle 214 moves from one program parameter to the next as the pen 102 (FIG. 1) moves. In this case, the rectangle 214 moves up and down the screen display as the pen 102 (FIG. 1) moves up and down the surface of the digitizer display screen 104. The use of the rectangle 214 or other method of highlighting (not shown) allows the physician or medical specialist to accurately select a particular object from among many densely packed objects.

When the telemetry head 118 (FIG. 2) is sufficiently close to the implantable medical device 116 (FIG. 2) to establish a telemetry link, medical data sensed by the implantable medical device 116 (FIG. 2) can be passed via the telemetry link as described above. Current measurements of medical data preferably are displayed in the upper window 198 of most screen displays.

Normally, four channels of information will be simultaneously displayed. The four channels are a surface ECG channel 226, a marker data channel 228, an atrial IEGM (AIEGM) channel 230, and a ventricular IEGM (VIEGM) channel 232. The current medical data is motionless until updated by a left to right sweep of a sweep bar 234.

Figure 5:
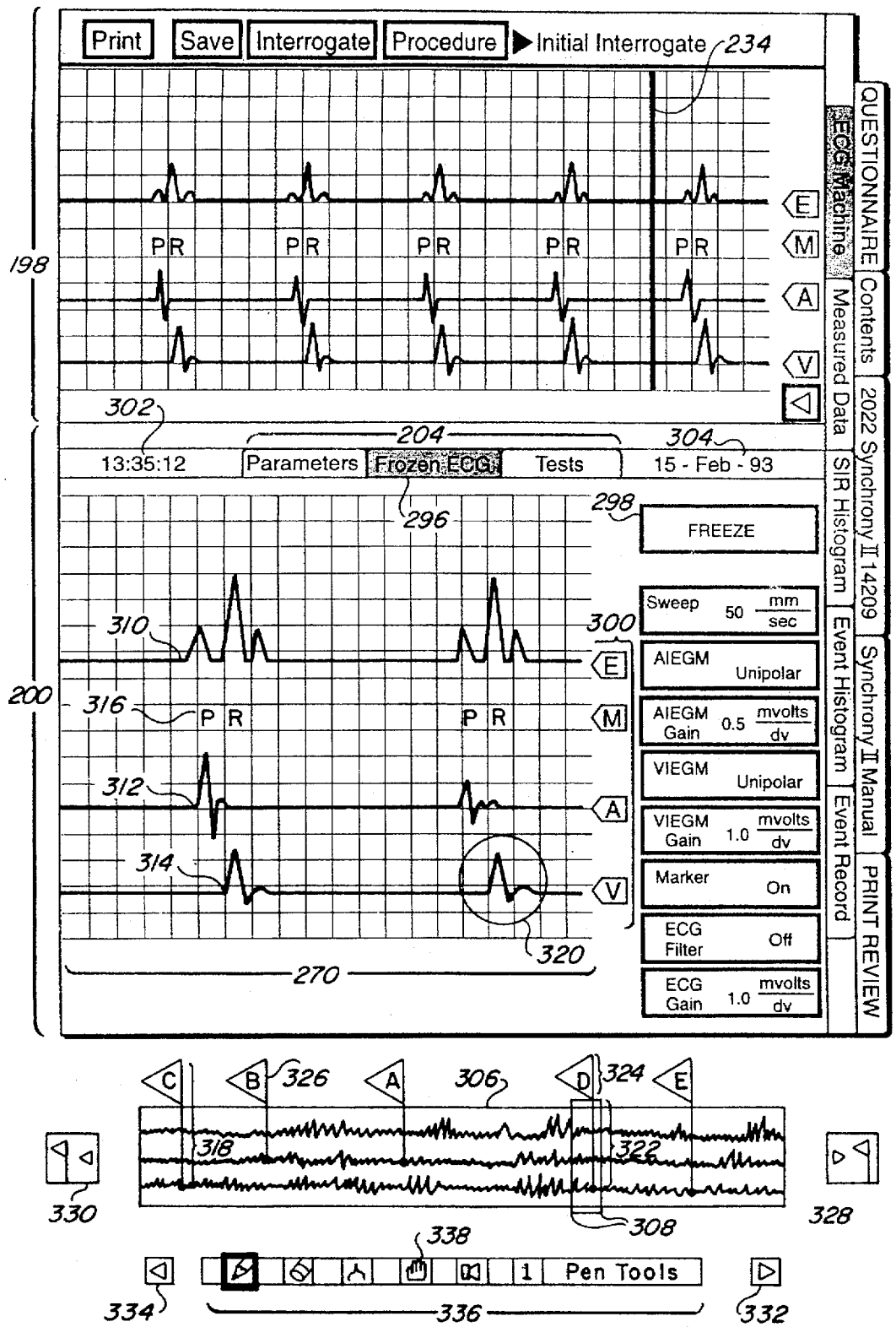
FIG. 5 is a sample screen display on the digitizer display screen with real-time data in the upper window and frozen data in the lower window.

In addition to the display of current medical measurements, the tablet computer 100 (FIG. 1) can be used to examine stored medical measurements. In FIG. 5, the upper window 198 is displaying current medical data and is being updated by the sweep bar 234. Tapping a frozen ECG button 296 causes a portion of the patient data scroll to be displayed in the lower window 200. The patient data scroll preferably includes the data received by the tablet computer 100 from the surface ECG channel 226, the marker data channel 228, the frozen AIEGM channel 230, and the frozen VIEGM channel 232. Tapping a freeze button 298 copies the most recent two minutes of the patent data into the lower window 200.

Frozen ECG machine controls buttons 300 are on the right side of the lower window 200. An indication of time 302 is provided to the left of the horizontal tabs 204, which displays the time of measurement of the portion of the patient data scroll displayed at the left edge of the lower window 200. An indication of date 304 is provided to the right of the horizontal tabs 204 if the patient data scroll was recorded on a date other than the current date.

Below the lower window 200 is a compressed buffer overview 306 and an indication of position 308. The compressed buffer overview 306 shows a view of the patient data scroll which has been shrunk to fit into the window allocated to the compressed buffer overview 306. The rendition reflects the relative positions and gains of a frozen surface ECG channel 310, a frozen AIEGM channel 312, and a frozen VIEGM channel 314 (all shown in lower window 200). A frozen marker data channel 316 (shown in lower window 200) is not reproduced in the compressed buffer overview 306.

An indication of position 308 is provided to indicate the currently displayed portion of the patient data scroll. A flag 318 is added to the compressed buffer overview 306 whenever an annotation 320 is created in order to aid in locating the relevant portion of the patient data scroll. The flag 318 is comprised of a flagstick 322 and a pennant 324. The base of the flagstick 322 points to the position in the compressed buffer overview 306 representative of the location of the annotation 320. The pennant 324 contains a unique symbol 326 to identify the annotation 320. In the preferred embodiment a letter of the alphabet is used, starting with "A" for the first annotation and "B" for the second. The unique symbol 326 preferably does not contain information indicative of the type of annotation. The unique symbols 326 preferably are not reordered or reissued if an annotation is deleted.

A flag jump right button 328 is provided to the right of the compressed buffer overview 306 and a flag jump left button 330 is provided to the left of the compressed buffer overview 306. Tapping the flag jump right button 328 causes the undisplayed flag located nearest to the right side of the currently displayed portion of data to be displayed in the lower window 200. Tapping the flag jump left button 330 causes the undisplayed flag located nearest to the left side of the currently displayed portion of data to be displayed. A "page forward" button 332 and a "page back" button 334 are provided on either side of a pen tool icon bar 336. The page forward button 332 advances the patient data scroll one visible segment 270. Conversely, the page back button 334 moves the patient data scroll one visible segment 270 to the left.

An alternative method of changing the displayed portion of the compressed buffer overview 306 is to tap the pen 102 (FIG. 1) on the flag pennant 324. This moves the patient data scroll so that the selected flag's annotation and the associated segment of patient data scroll is displayed in the lower window 200.

Another tool for making small horizontal adjustments to the patient data scroll is provided on the pen tool icon bar 336. Tapping a hand tool icon 338 on the pen tool icon bar 336 turns the pen 102 (FIG. 1) into the hand tool. When the pen 102 (FIG. 1) is functioning as the hand tool, placing the pen 102 (FIG. 1) anywhere on the lower window 200 and then dragging the pen 102 (FIG. 1) horizontally causes the patient data scroll to move in the horizontal direction with the pen 102 (FIG. 1) as if the pen 102 (FIG. 1) was holding onto the patient data scroll. The pen 102 (FIG. 1) continues to function as the hand tool until the hand tool icon 338 is tapped again on the pen tool icon bar 336.

The tablet computer 100 preferably permits the physician to create both ink annotations and footnote annotations on the patient data scroll as described in the aforementioned '367 application. Briefly, an ink annotation allows the physician to "write" directly on the displayed data using the digitizer pen, while a footnote annotation allows the physician to enter text into a footnote window associated with a footnote marker.

Figure 6:
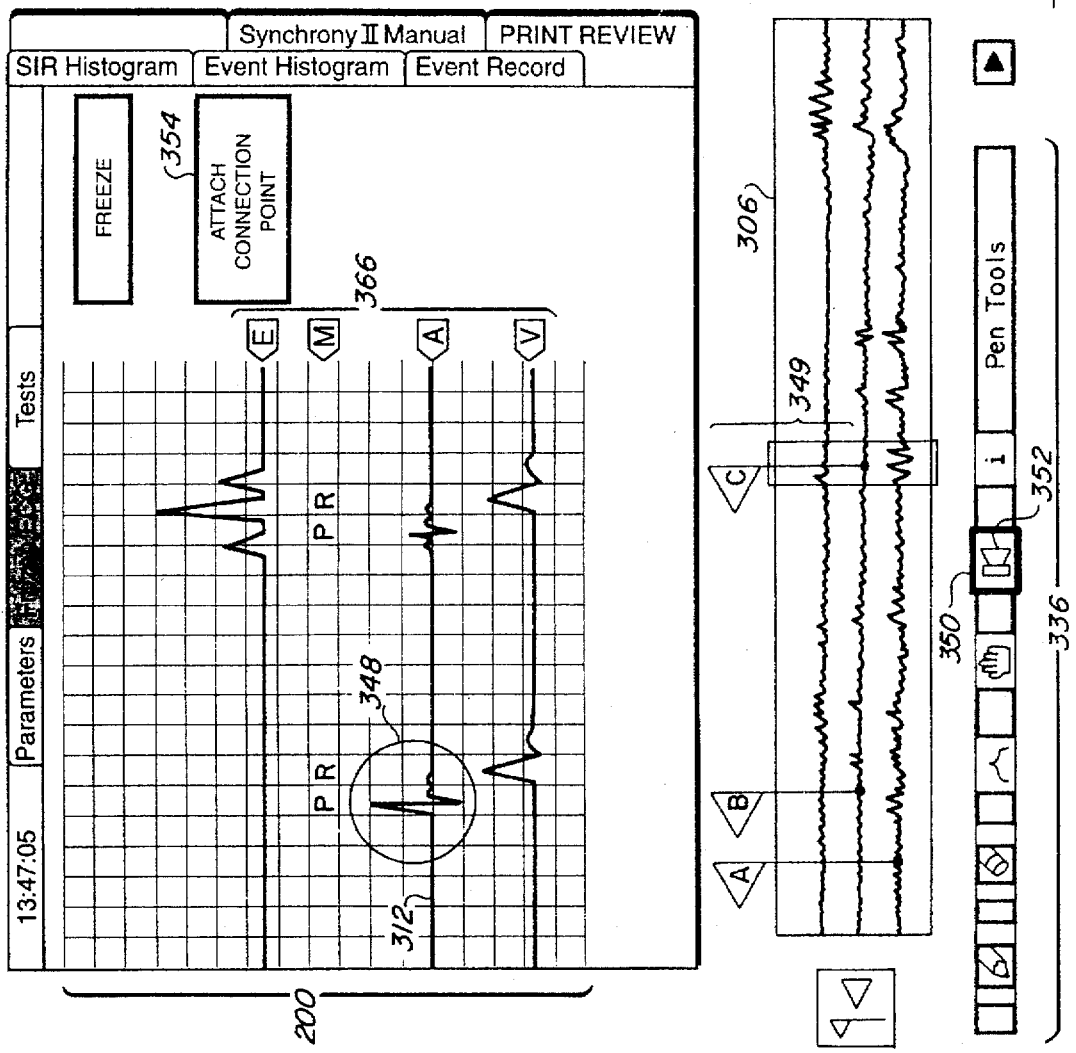
FIG. 6 is a portion of a screen display on the digitizer display screen showing the designation of a connection point during the recording of a voice annotation in accordance with the present invention.

Turning to FIG. 6, the manner by which the physician or medical specialist can create voice annotations in accordance with the present invention is described. Before creating a voice annotation, the physician has annotated the frozen AIEGM channel 312 with a circular ink annotation 348 around one AIEGM waveform using the ink tool as described in the '367 application. A flag 349 with a unique identifier "C" was added to the compressed buffer overview 306 to mark the location of the circular annotation 348.

Voice annotation of the medical data preferably is initiated by tapping the pen 102 (FIG. 1) onto a voice annotation tool icon 350. After tapping the voice annotation tool icon 350, a dark square 352 highlights the voice annotation tool icon 350 indicating that the tablet computer is in the voice annotation mode. The physician preferably designates a "connection point" when creating a voice annotation in order to link the voice annotation to a particular portion of the patient data. The connection point allows the annotation to follow the appropriate segment of medical data when the channel of medical data is moved.

After tapping the voice annotation tool icon 350, the tablet computer 100 reminds the physician with a pop-up message 354 to designate a connection point. The tablet computer 100 expects that the next input from the pen 102 (FIG. 1) will designate the connection point. Preferably, the physician designates the connection point by tapping a location in the lower display window 200.

Figure 7:
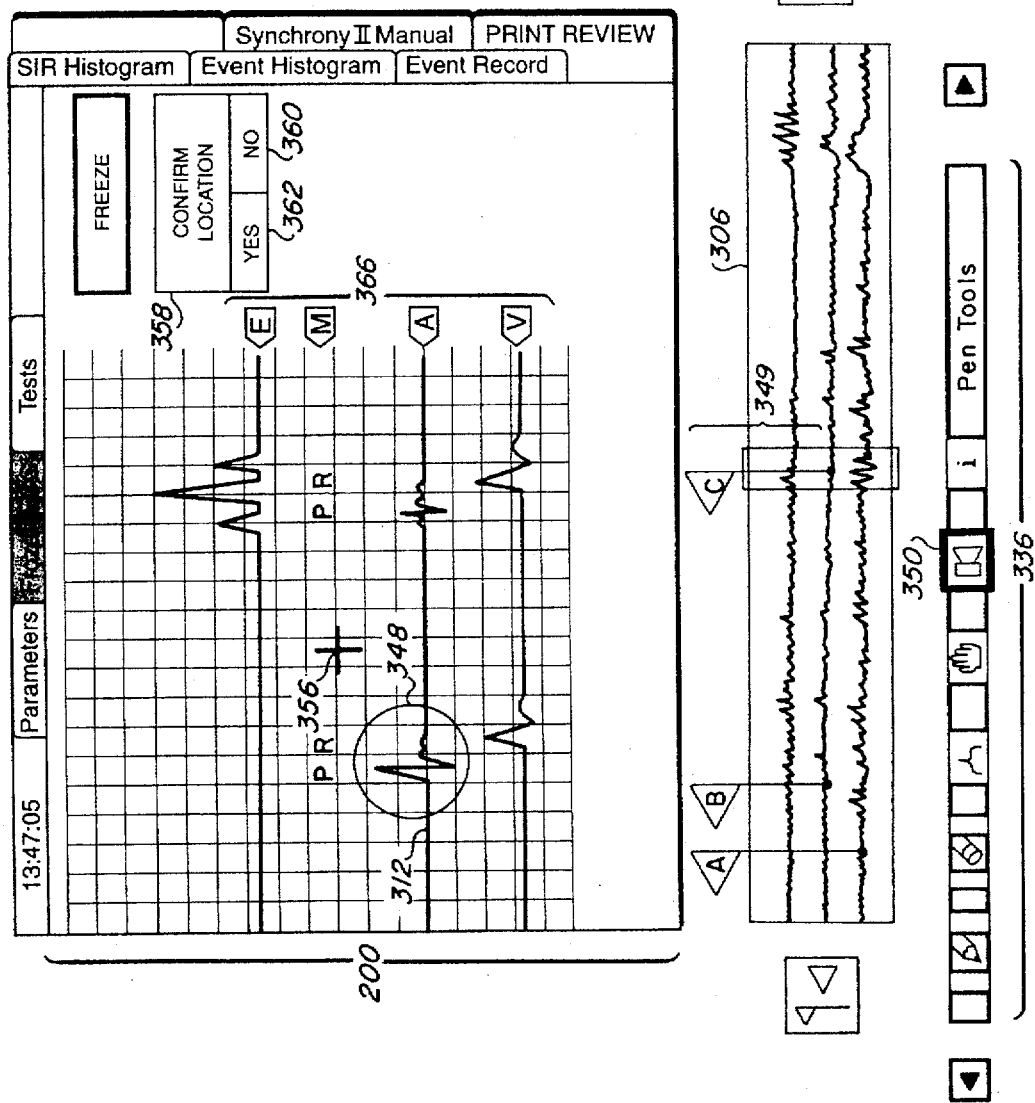
FIG. 7 is a portion of a screen display on a digitizer display screen during the confirm cycle of the designation of a connection point.

As shown in FIG. 7, the point at which the physician tapped the lower display window 200 preferably is indicated with a set of cross hairs 356. A confirmation window 358 is preferably provided in order to confirm the designation of the connection point. Tapping a confirmation-no button 360 with the pen 102 (FIG. 1) requests another opportunity to designate a connection point. The selection of a connection point is completed by tapping a confirmation-yes button 362.

In an alternative embodiment (not shown), the confirmation cycle can be eliminated to streamline the designation of the connection point.

Figure 8:
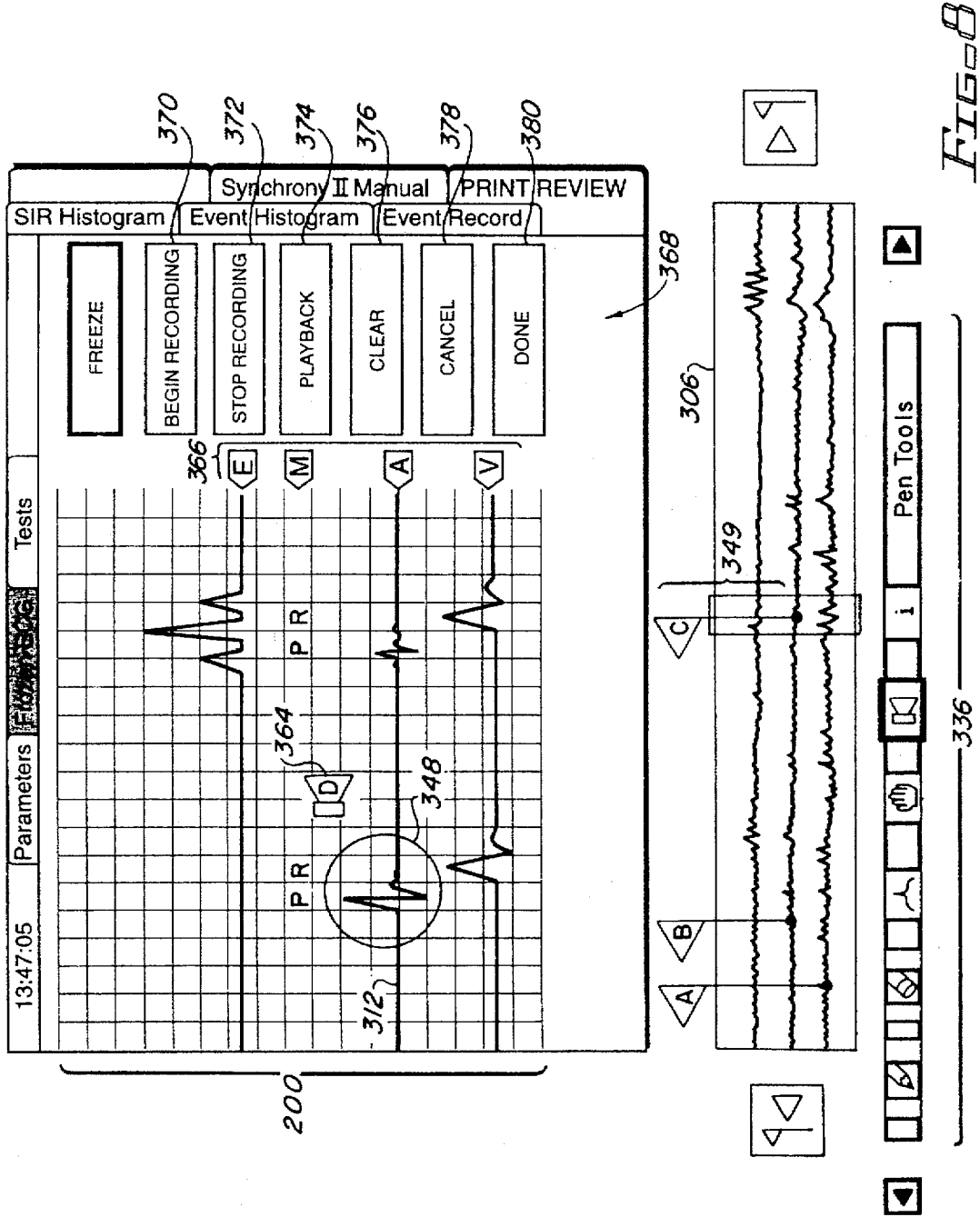
FIG. 8 is a portion of a screen display on the digitizer display screen showing a control window for use when recording a voice annotation.

Turning to FIG. 8, once the selection of a connection point is complete, a voice annotation marker 364 preferably appears at the connection point. In this case, the voice annotation marker 364 is labeled with the letter "D." This preferably is the same letter as is used to label a corresponding flag in the compressed buffer overview 306 (described below in connection with FIG. 9) when recording of the voice annotation is complete. The voice annotation marker 364 preferably is shaped like a speaker in order to indicate to the physician that the marker 364 relates to a voice annotation rather than another type of annotation (e.g., an ink or footnote annotation).

If the voice annotation pertains to one particular channel of medical data and the physician or medical specialist wishes to identify the channel being annotated, an ink annotation such as an arrow or circle annotation 348 can be added to highlight the subject of the voice annotation. FIG. 8 serves as an example of this combination of ink and voice annotations for a particular piece of medical information. Of course, a voice annotation can be added to the patient data scroll without an accompanying ink annotation.

After the physician has confirmed the connection point, a control window 368 appears in the lower window 200 as shown in FIG. 8. Tapping a begin recording button 370 preferably causes the tablet computer 100 to begin recording voice data. The physician preferably taps the stop recording button 372 to stop recording voice data. If the physician wishes to add to the voice annotation after tapping the stop recording button 372, the physician presses the begin recording button 370 again to continue recording. In a preferred embodiment, this process may be repeated any number of times.

An example of recording a voice annotation is now given for purposes of illustration. The physician first taps the begin recording button 370 and then speaks the words, "one AIEGM pulse had an unusually high voltage differential of about one-point-five millivolts." The physician then taps the stop recording button 372. Digital data corresponding to the sounds spoken by the physician preferably are stored in the general memory unit 148 (FIG. 1) of the tablet computer 100 (FIG. 1).

The present invention can be used to record voice annotations of any length provided that the tablet computer has sufficient available memory to store the corresponding digital data. A voice annotation can include any type of spoken information, including, but is not limited to, progress made by a patient since the last visit, the success of a particular therapy, and the patient's status report distribution list. The voice annotation could also include non-spoken sounds such as computer generated sounds. (The term "digital voice data" used herein to refer to the digital data of a voice annotation is meant to include the digital data corresponding to such non-spoken sounds.)

The physician taps a playback button 374 to cause the voice annotation to be played back for review.

Tapping a clear button 376 deletes all previously entered voice data for the current voice annotation, but leaves the control window 368 on the display screen so that the physician can compose a new message. A confirm cycle preferably is provided when the clear button 376 is pressed in order to prevent the accidental deletion of voice data.

Tapping a cancel button 378 closes the control window 368 and ends the voice annotation input step without saving the voice annotation. A confirm cycle preferably is provided when the cancel button 378 is pressed in order to prevent the accidental deletion of voice data.

Tapping a done button 380 preferably will end the input step, save the voice data input, and add another flag (described below in connection with FIG. 9) to the compressed buffer overview 306.

The playback button 374, the clear button 376, the cancel button 378, and the done button 380 preferably are inactive while the physician is recording a voice annotation. That is, these buttons preferably are inactive between the time when the physician taps the begin recording button 370 and the time when the physician taps the stop recording button 372. In an alternative embodiment (not shown), the playback button 374, the clear button 376, the cancel button 378, and the done button 380 are shaded while the physician is recording a voice annotation in order to indicate that they are inactive. In another alternative embodiment (not shown), the playback button 374, the clear button 376, the cancel button 378, and the done button 380 are hidden while the physician is recording a voice annotation.

Figure 9:
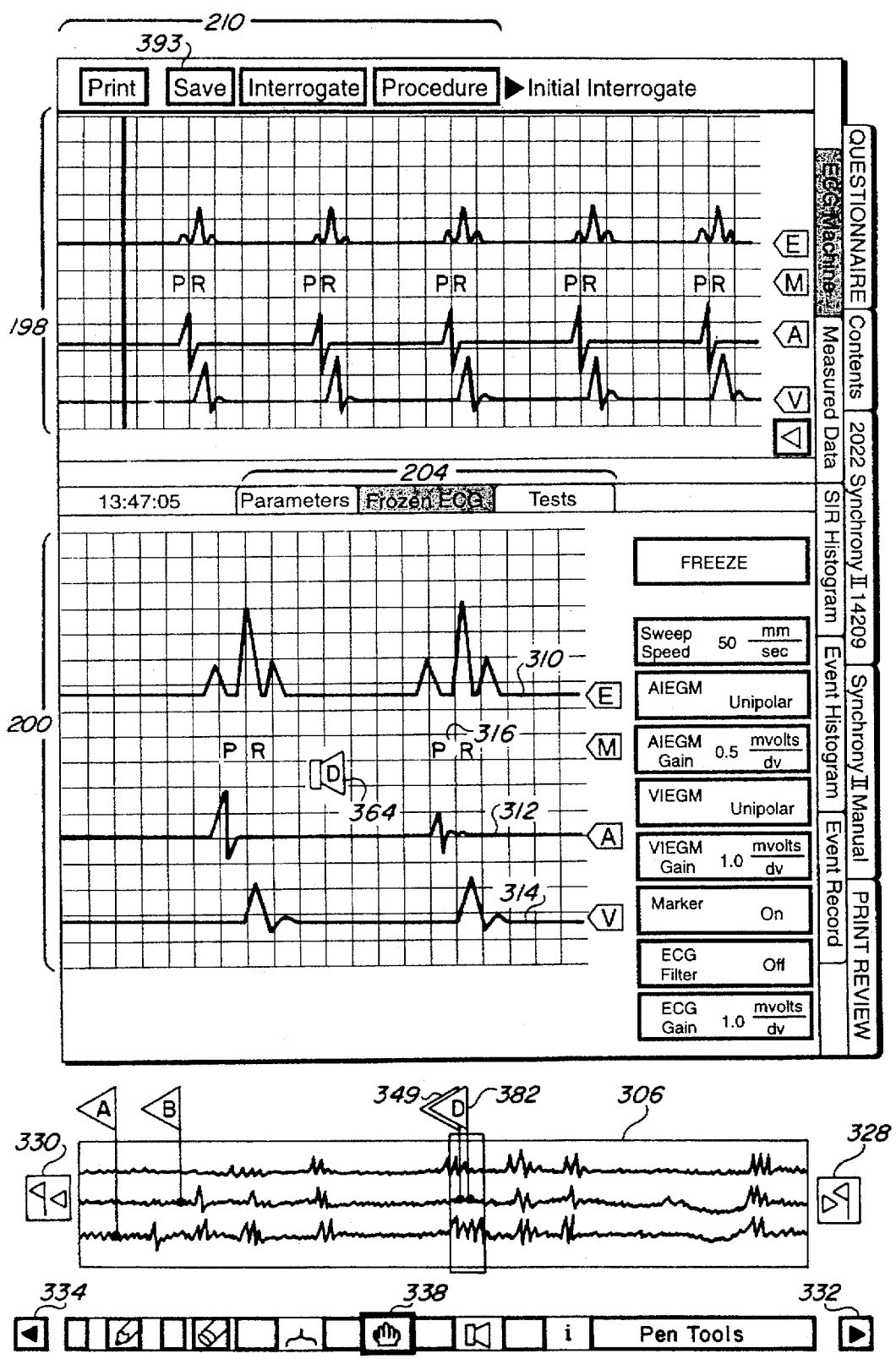
FIG. 9 is a portion of a screen display on the digitizer display screen after a voice annotation has been created.

The result of tapping the done button 380 appears in FIG. 9, with a flag 382 labeled "D" marking the new voice annotation. The flag 382 substantially covers the flag 349 labeled "C" (mostly covered and not visible) marking the ink tool annotation. After the done button 380 has been tapped, the physician can move to other portions of the patient data scroll using the flag jump right button 328, the flag jump left button 330, the page forward button 332, the page back button 334, and the hand tool 338 as described above. The physician can also move to a particular flag by tapping on that flag in the compressed buffer overview 306 as described above. The physician can move to other portions of the patient data scroll and then create additional voice annotations. The physician can also move to and select a previously recorded voice annotation in order to modify it.

Figure 10:
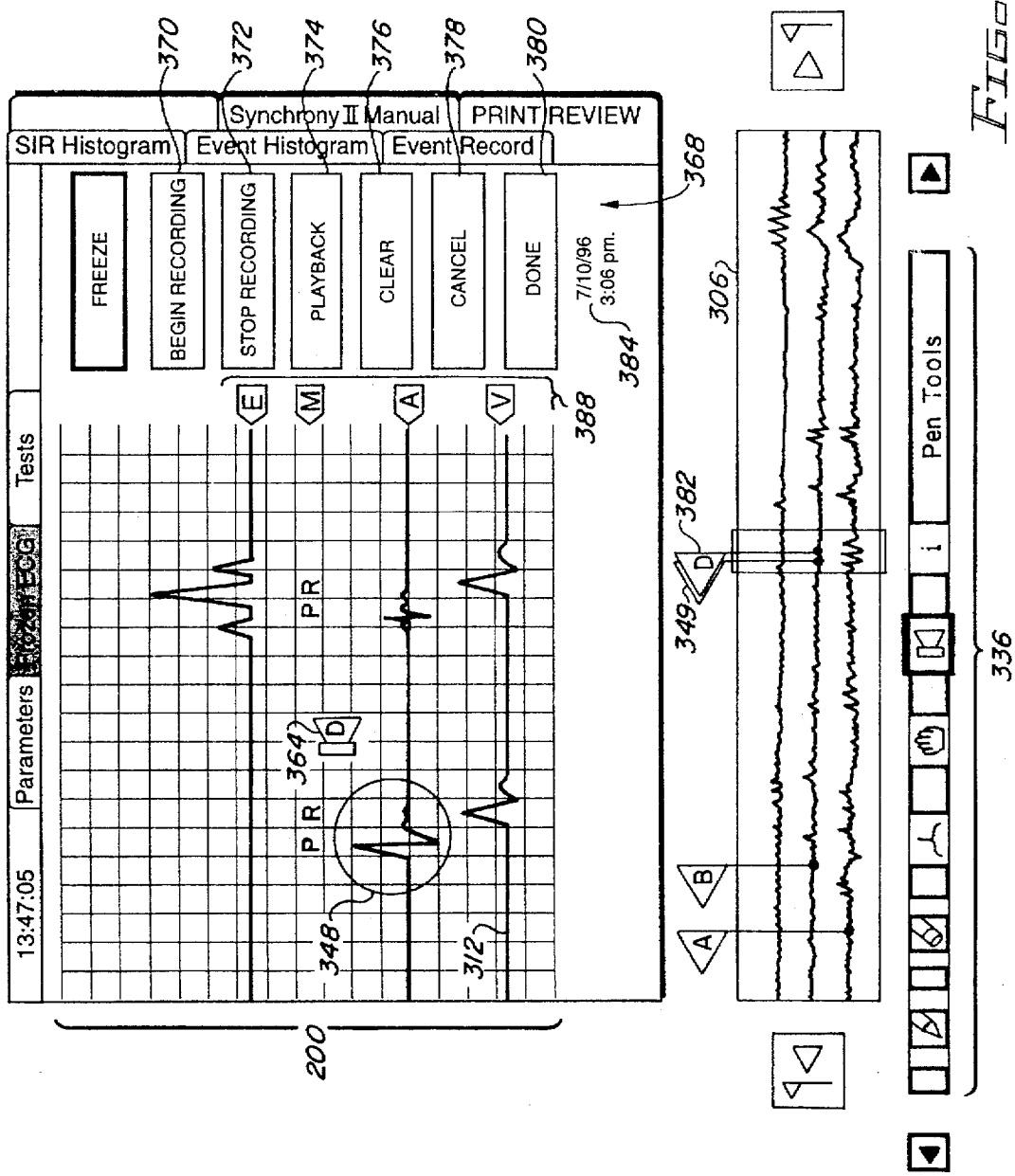
FIG. 10 is a portion of a screen display on the digitizer display screen after the voice annotation of FIG. 9 has been selected for display.

FIG. 10 shows the display screen after the physician has selected the voice annotation marker 364 corresponding to a previously recorded voice annotation. The screen is similar to the screen of FIG. 8 except that the flag 382 and a date and time of recording 384 appear on the display screen. The date and time of recording 384 preferably show the date and time at which the voice annotation was recorded. The physician preferably can add further voice data to the voice annotation using the control window 368. In particular, tapping the begin recording button 370 permits the physician to record voice data which preferably is added to the end of the previous voice annotation, rather than replacing the previous voice annotation. When the physician is finished recording the additional voice data, he or she taps the stop recording button 372.

Tapping the playback button 374 preferably causes the voice annotation to be played back, including any newly recorded voice data.

Tapping the clear button 376 preferably deletes all voice data entered for a particular voice annotation since that voice annotation was selected. That is, tapping the clear button 376 preferably does not effect any voice data recorded before the voice annotation marker 364 was selected for display. A confirm cycle preferably is provided when the clear button 376 is pressed in order to prevent the accidental deletion of voice data. As is the case when recording a new voice annotation, the control window 368 preferably remains displayed after the clear button 376 is pressed.

Tapping the cancel button 378 preferably ends the display of the voice annotation without saving the voice data recorded while the voice annotation marker 364 was selected. Previously recorded voice data preferably is not effected by tapping the cancel button 378. A confirm cycle preferably is provided when the cancel button 378 is pressed in order to prevent the accidental deletion of voice data.

Tapping the done button 380 preferably ends the display of the voice data and preferably saves any additional voice data that was recorded while the voice annotation marker 364 was selected. If any new voice data has been recorded, then the date and time of recording of the new voice data preferably is saved.

Although FIGS. 6–10 illustrate the creation of a single voice annotation, the physician can create two or more voice annotations which appear on the same screen display.

Figure 11:
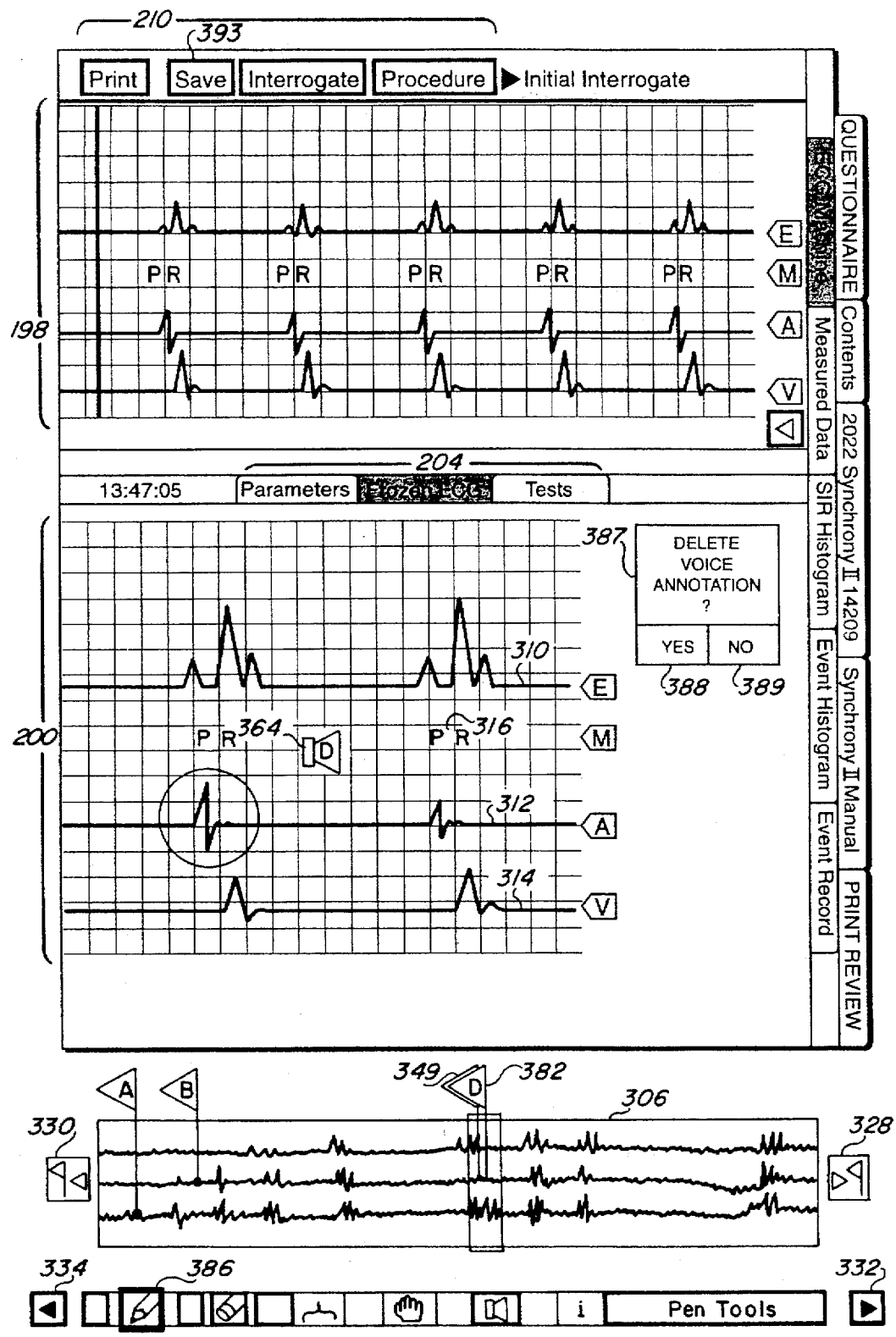
FIG. 11 is a portion of a screen display on the digitizer display screen illustrating the deletion of a voice annotation using an eraser tool.

Referring to FIG. 11, a voice annotation can be deleted by touching the voice annotation marker 364 with the pen tip 110 (FIG. 1) while the pen 102 (FIG. 1) is an eraser tool. To make the pen 102 (FIG. 1) an eraser tool, the user taps an eraser tool icon 385. FIG. 11 shows the display screen after the user has tapped the eraser tool icon 385 and then tapped the voice annotation marker 364. The eraser tool icon 385 is highlighted by a box 386, and a confirmation window 387 having a "YES" button 388 and a "NO" button 389 is displayed in the lower window 200 to prevent accidental erasure of a voice annotation. If the user taps the "NO" button 389, the voice annotation is not deleted and the pen 102 (FIG. 1) no longer acts an eraser tool. If the user taps the "YES" button 388 then the voice annotation marker 364 is deleted.

Figure 12:
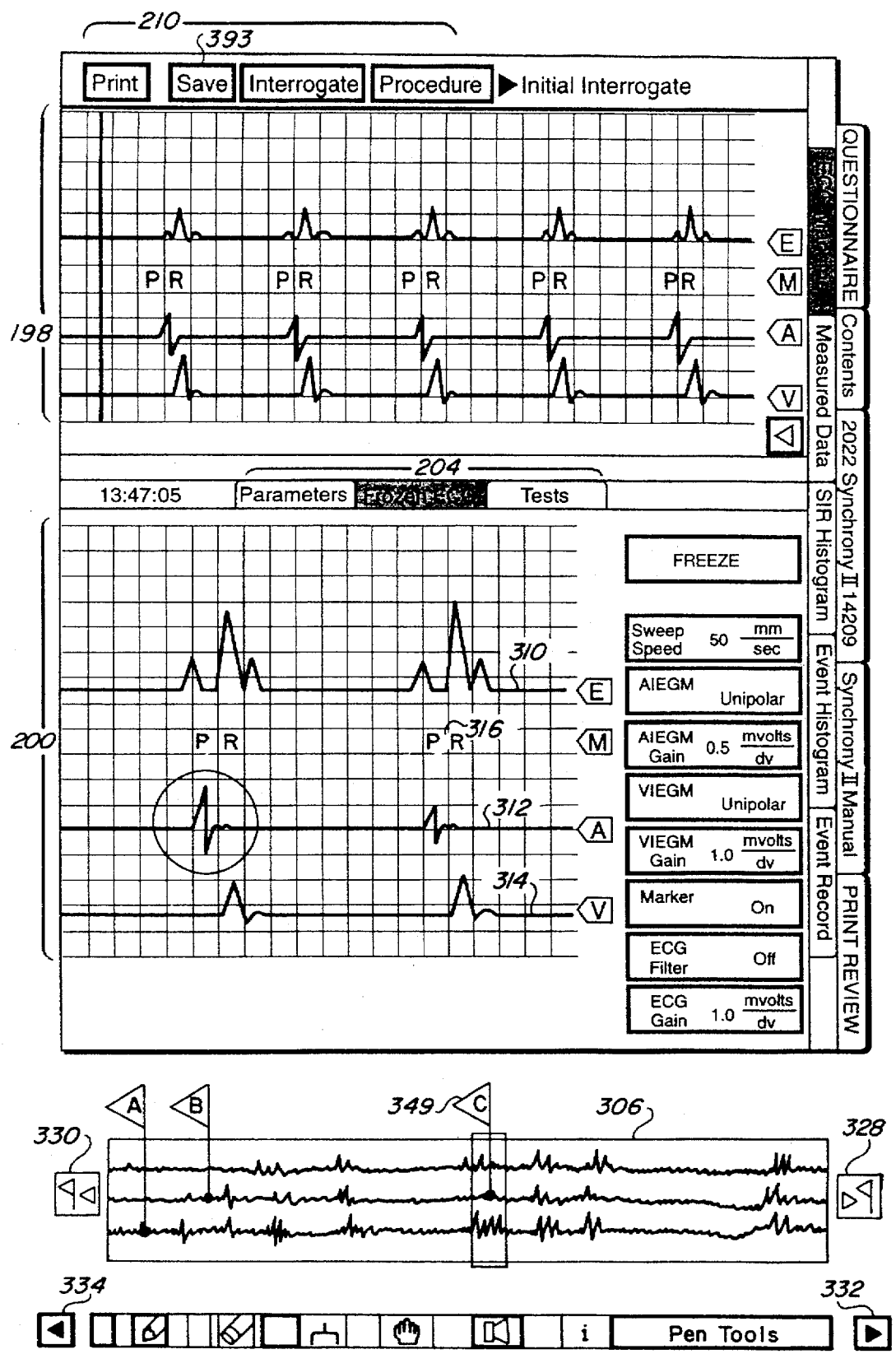
FIG. 12 is a portion of a screen display on the digitizer display screen depicting the display after a voice annotation has been deleted using the eraser tool.

As shown in FIG. 12, deleting the voice annotation removes the voice annotation marker 364 from the lower window 200. The flag 382 labeled "D" corresponding to the deleted voice annotation is removed from the compressed buffer overview so that the flag 349 labeled "C" becomes visible. Save requests made after the deletion of the voice annotation will not include the voice annotation.

Figure 13:
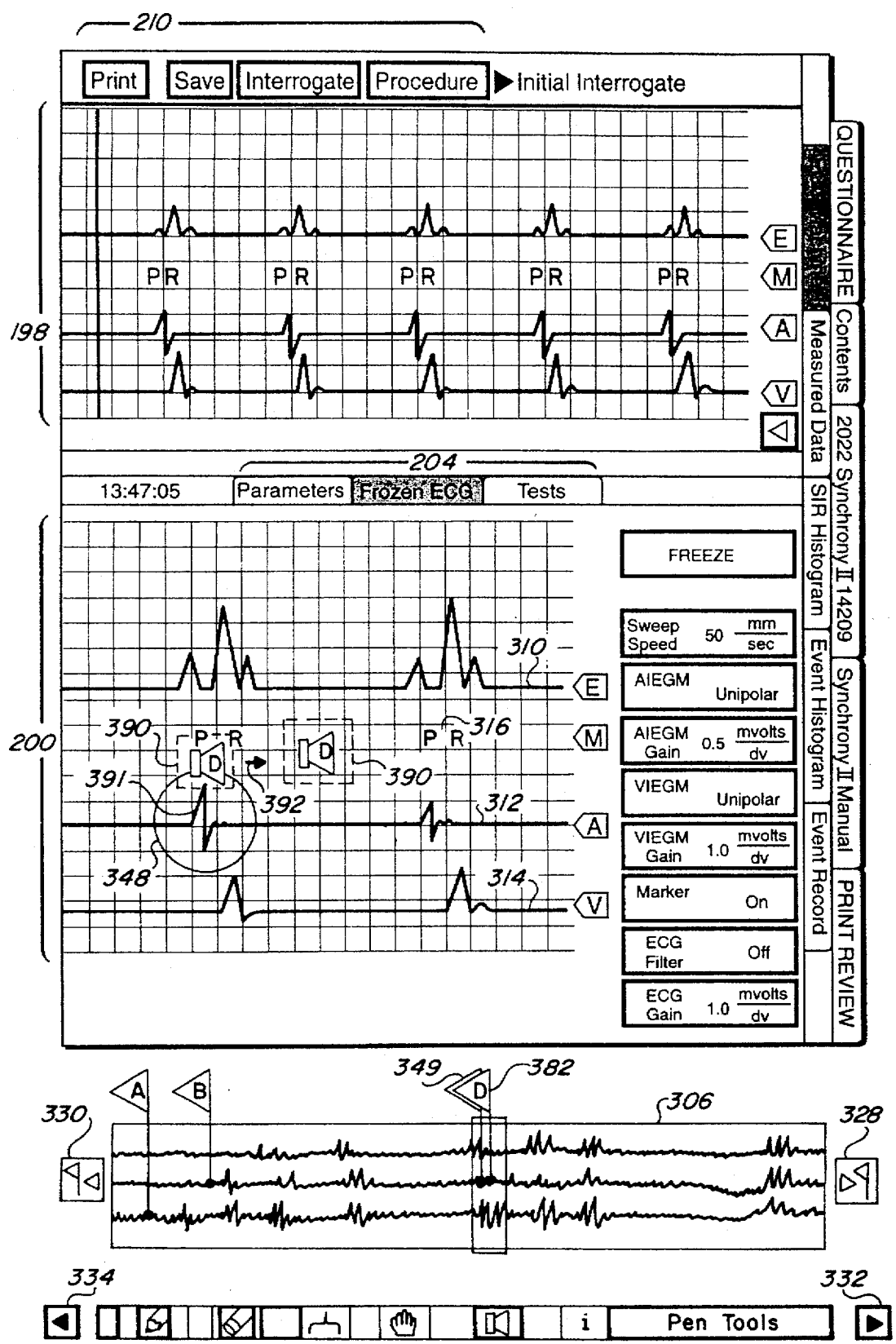
FIG. 13 is a portion of a screen display on the digitizer display screen illustrating movement of a voice annotation.

Referring to FIG. 13, a voice annotation may be moved with a press and hold gesture. Pressing the pen 102 (FIG. 1) upon the voice annotation marker 364 in the lower window 200 for a predetermined minimum amount of time (preferably about one-half second) is recognized by the tablet computer 100 (FIG. 1) as the start of a press and hold gesture. Upon recognition, the tablet computer 100 (FIG. 1) places a marquee such as a blinking double line box 390 around the selected voice annotation marker 364.

After the marquee appears, the marquee and the voice annotation marker 364 it surrounds will "float". Floating means that the selected item will follow the pen 102 (FIG. 1) until the physician or medical specialist presses and holds the pen 102 (FIG. 1) for at least one-half second to affix the selected item to a new location. The marquee disappears when the item has been affixed. To move the selected item to a new location, the physician or medical specialist touches the selected item with the pen 102 (FIG. 1) and drags to pen 102 (FIG. 1) to the new location. The selected item continues to float until affixed, so the movement of the selected item does not need to happen within a single drag movement of the pen 102 (FIG. 1). Consequently, while an item is floating, the physician or medical specialist may move the scroll using other gestures such as the various flick gestures or other aids such as the page forward button 332 or the page back button 334.

Figure 14:
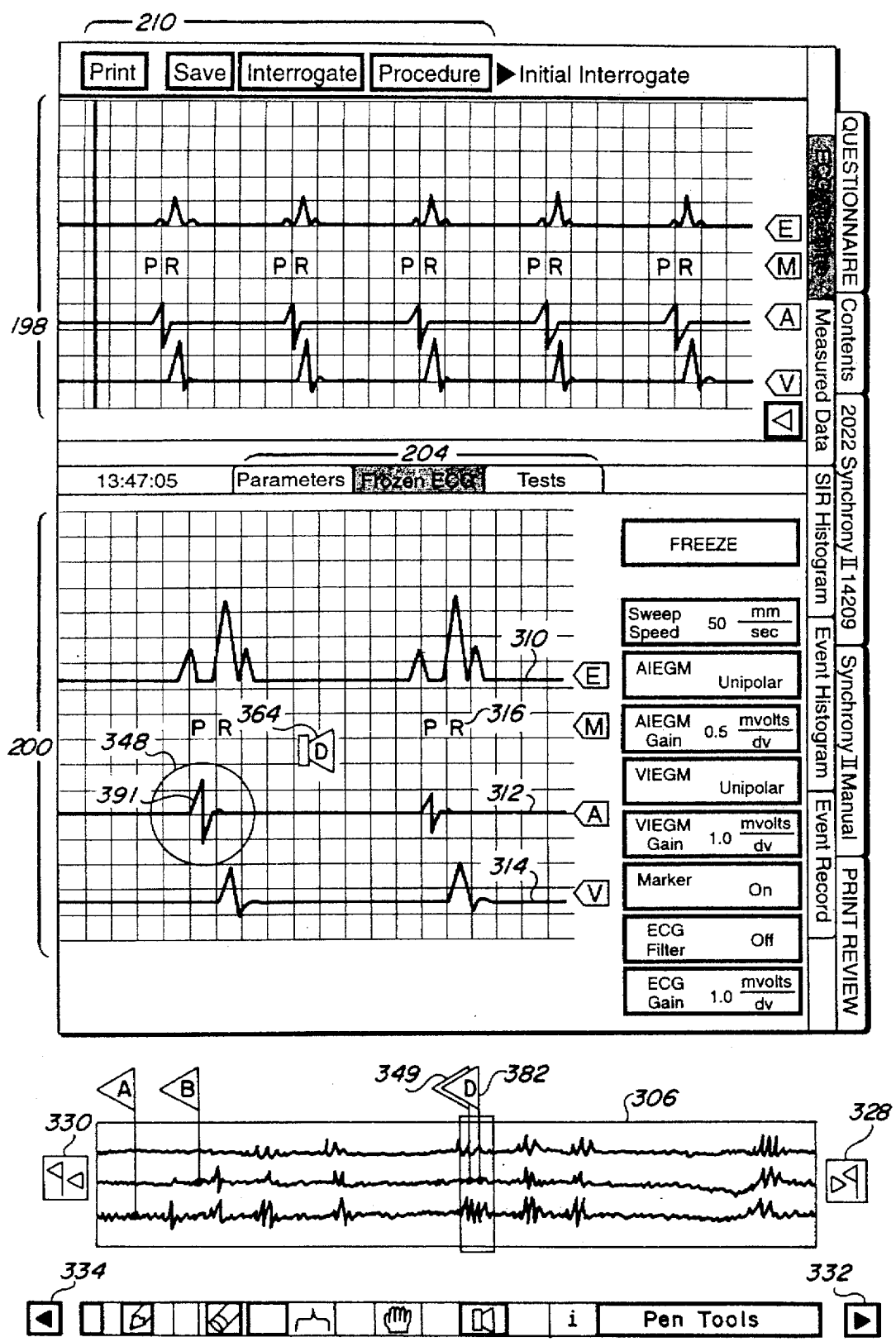
FIGS. 14 is a portion of a screen display on the digitizer display screen depicting the display after a voice annotation has been moved.

As illustrated in FIG. 13, the voice annotation marker 364 was originally placed so that it covered part of a pulse 391 and part of the ink annotation 348. Arrow 392 indicates that the user has dragged the voice annotation marker 364 to the right so that it no longer covers the pulse 391 and ink annotation 348. FIG. 14 shows the voice annotation marker 364 after the user has released it. The pulse 391 and the ink annotation 348 are now clearly visible.

In an alternative embodiment (not shown), the voice data recorded by the tablet computer 100 are "compressed" before being stored in order to reduce the amount of data that must be saved for a voice annotation. Compressing the voice data, however, has the disadvantage of increasing the amount of time necessary to record or playback a voice annotation. Techniques for compressing digital data are well known in the art.

Special software programs called voice recognition engines are known and have been applied to personal computers. Such engines allow voice input to be recognized as words and then manipulated as digital data. In an alternative embodiment (not shown), the tablet computer 100 is programmed using a voice recognition engine so that the words spoken by the physician while recording a voice annotation are recognized by the tablet computer 100 and converted to digital data. In this embodiment, the words spoken by the physician appear in text form in a window (not shown) on the display screen of the tablet computer 100. The physician preferably uses a conventional text editor to edit the text displayed in the display window. A disadvantage of using voice recognition software is that currently available voice recognition engines are able to recognize only a relatively limited number of words. This embodiment may be advantageous, however, in situations where only a limited number of words are used by the physician.

A "save" function creates a copy of all information and annotations for a particular patient. Referring back to FIG. 9, a save button 393 is one of the series of buttons 210 on the top of many screen displays. The save function is useful when the physician or medical specialist does not have time to examine and annotate frozen medical data and wishes to do so later. For example, some medical procedures cause discomfort. The physician or medical specialist may wish to continue the exam rather than continue annotating the results while the patient is uncomfortable. In some situations, the patient's situation may change too quickly to fully annotate the results such as when the tablet computer 100 (FIG. 1) is used in an emergency room or operating theater. A third possibility is that the physician or medical specialist may want to capture the complete set of data for discussion with peers or students. A fourth possibility is that the physician may wish to save the data set, including all voice annotations, so that a medical specialist or other appropriate personnel can transcribe the voice annotations and carry out any instructions recorded on the voice annotations.

The physician or medical specialist preferably is not allowed to select which screen displays, patient data scrolls, or other material is saved. All information that is relevant to the patient preferably is saved. The physician or medical specialist who requests another save after making just one minor change to one screen display preferably saves an entire set of data, display screens, and related material. Although this may seem inefficient, the advantages of speed, simplicity of commands, and assurance of capturing all necessary information outweigh the disadvantage of storing some unwanted or redundant information.

Figure 15:
FIG. 15 is an illustrative screen display used to manage previously saved sets of screen displays and medical data.

Turning now to FIG. 15, the save catalog menu lists the sets of saved data. The sets of saved data are identified by a saved set name 394 comprising a model number and a serial number of the implantable medical device coupled with a date and a time when the data was saved. If known to the tablet computer 100 (FIG. 1), a name of the patient is provided as an aid to physician or medical specialist in finding a particular patient's data.

Tapping a review button 395 and then tapping on the saved set name 394 of the desired set of saved data will return the physician or medical specialist to the screen display that was open when the save request was made. Tapping a delete button 396 and then tapping on a save catalog line number 397 causes the letters 'DEL" appear in place of the selected save catalog line number 397. Tapping the letters "DEL" will cause the letters "DEL" to disappear, and the selected save catalog line number 397 to reappear. In this case the save catalog line number 397 that can reappear is "3)".

Figure 16:
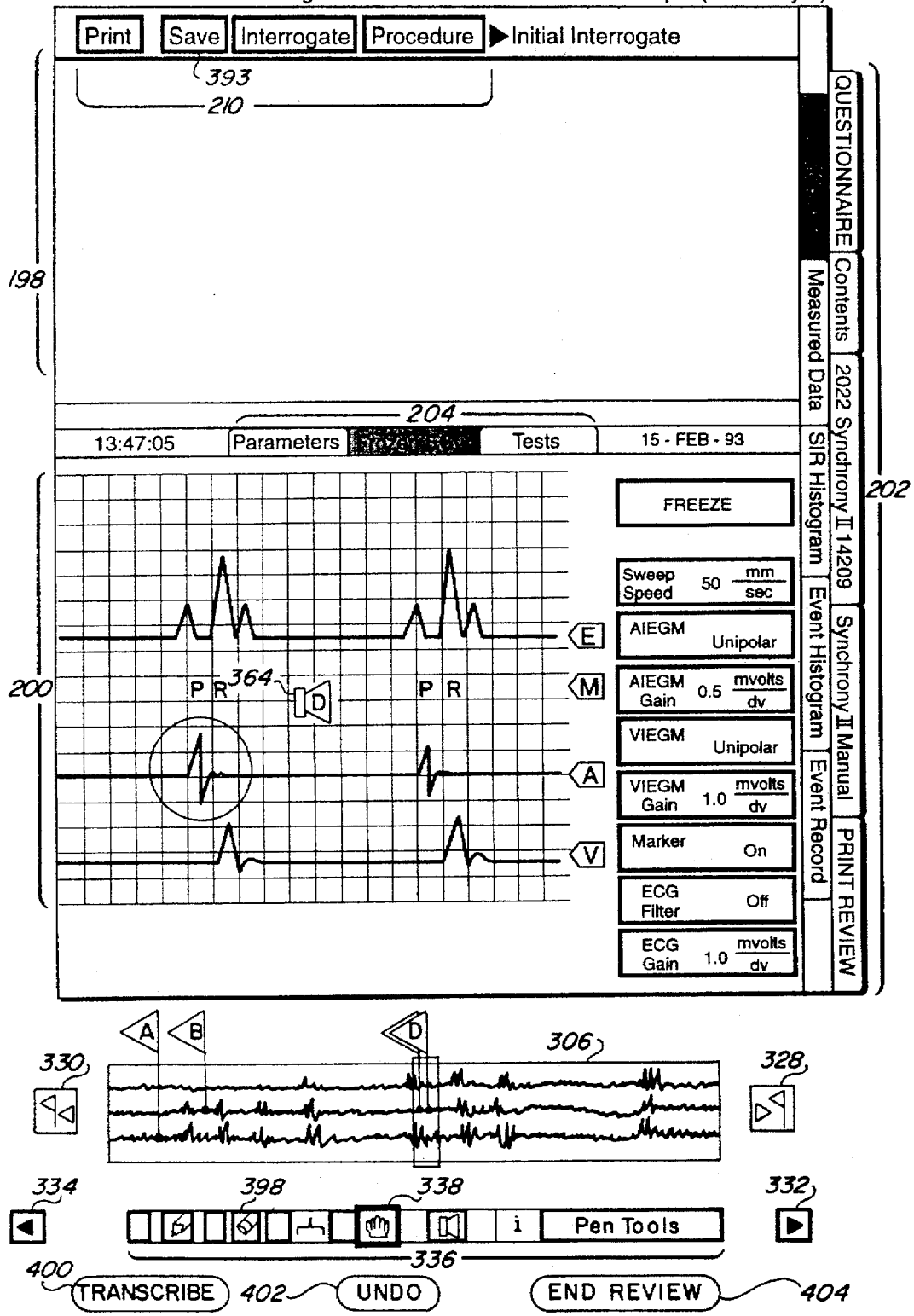
FIG. 16 is an illustrative screen display for review of a set of saved data, the screen display including a transcribe button.

Tapping the review button 395 places the tablet computer 100 (FIG. 1) in review mode as shown in FIG. 16. The physician or medical specialist does not need to learn a new set of commands to operate the review mode. The physician or medical specialist has a familiar screen display with the series of buttons 210. The physician or medical specialist can move to other screen displays through the use of the vertical tabs 202, or horizontal tabs 204.

Movement within the patient data in the lower window 200 is done through the physician's or medical specialist's choice of the page forward 332, page back 334, flag jump right 328, flag jump left 330, or through the use of the hand tool icon 338 found on the pen tool icon bar 336.

In accordance with the present invention, the physician or medical specialist may add new voice annotations, ink annotations, or footnote annotations. The new annotations will be marked by additional flags in the compressed buffer overview 306. The physician or medical specialist may erase existing annotations by using the pen 102 (FIG. 1) as the eraser tool after tapping an eraser tool icon 398.

In accordance with the present invention, during the review of saved data, a transcribe button 400, an undo button 402, and an end review button 404 preferably appear on the display screen in the review mode. The undo button 402 deletes all modifications made to that particular review screen display during the review of saved data. Tapping the undo button 402 does not affect changes made to other screen displays during the review session. Tapping the end review button 404 terminates the review session and stores all changes to the existing set of saved data.

Tapping the end review button 404 returns the display to the save catalog menu (as shown in FIG. 15). Subsequent review of this same saved data set will start at the screen display that the physician or medical specialist was viewing when the physician or medical specialist tapped the end review button 404. Subsequent reviews will show the annotations as modified during prior reviews of the same saved data.

Figure 17:
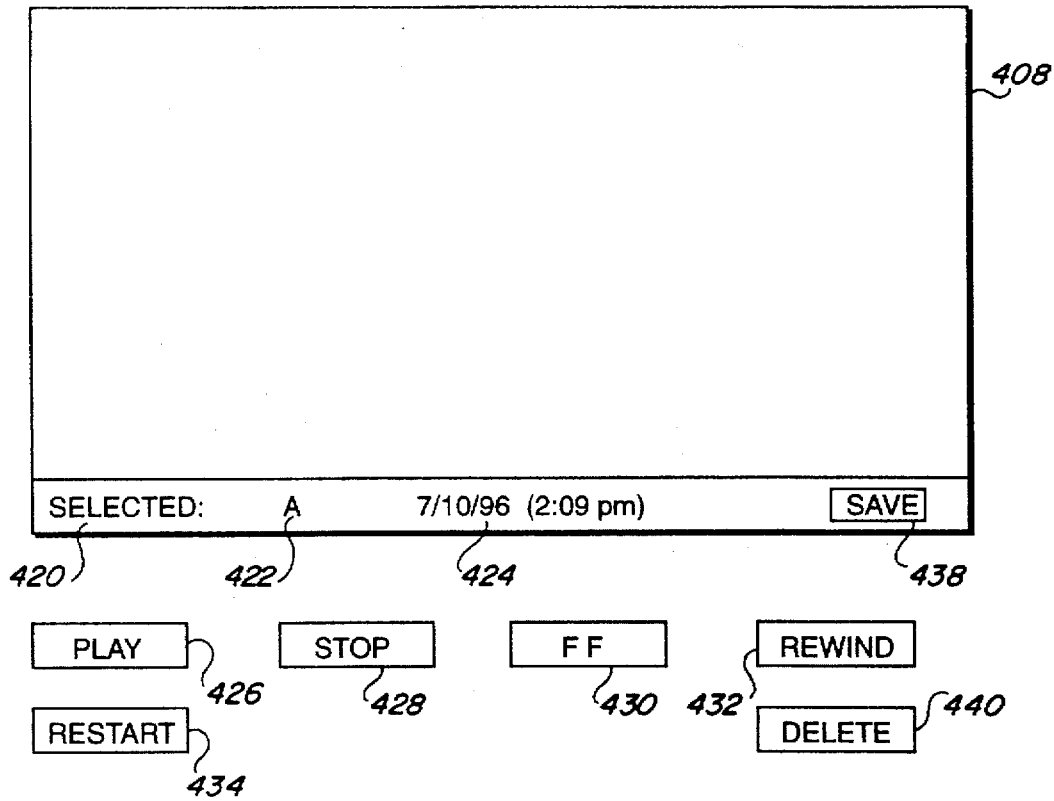
FIG. 17 is a preferred screen display used to select a voice annotation for transcription.

Tapping the transcribe button 400 causes a transcription menu 406 and a text window 408 to appear on the display screen as shown in FIG. 17. A list of all voice annotations associated with the data set preferably is displayed in the transcription menu 406. A voice annotation 410 preferably is identified by a flag letter 412 (preferably the letter of the flag associated with the voice annotation), a date and time of recording 414 (preferably the date and time at which the voice annotation 410 was created), and a transcription indicator 416. The transcription indicator 416 preferably is either "Y" or "N". As shown in FIG. 17, the transcription indicator 416 of the voice annotation 410 is "N", meaning that the voice annotation 410 has not been transcribed. A "Y" preferably is used to indicate that a voice annotation has been transcribed.

Voice annotations can be transcribed by the person who created the voice annotation (e.g., physician or medical specialist) or by any other appropriate person. A voice annotation is selected for transcription by tapping a transcribe button 418 and then tapping the voice annotation. In this case, the medical specialist has selected the voice annotation 410 for transcription. Because the voice annotation 410 has not been transcribed, no text appears in the text window 408. (If the voice annotation 410 had been partially or completely transcribed (not shown), the transcribed text preferably would appear in the text window 408.) A selection label 420 preferably informs the medical specialist which voice annotation has been selected by displaying a flag letter 422 and a date and time of recording 424.

A play button 426, a stop button 428, a fast-forward button 430, a rewind button 432, and a restart button 434 preferably are provided so that the medical specialist can listen to the voice annotation 410. The medical specialist taps the play button 426 to begin playback of the voice annotation 410, and taps the stop button 428 to stop playback of the annotation. If the medical specialist taps the play button 426 after tapping the stop button 428, the voice annotation 410 preferably is played back beginning at the point where playback was previously stopped. Tapping the restart button 434 preferably causes the voice annotation 410 to playback from the beginning of the voice annotation 410 rather than from the point at which the stop button 428 was last pressed. The medical specialist preferably can tap the restart button 434 anytime during playback in order to return to the beginning of the voice annotation 410. The fast-forward button 430 causes the playback to skip forward in the voice annotation 410, while the rewind button 432 causes the playback to skip back in the voice annotation 410.

The medical specialist preferably converts the voice annotation 410 into text using the keyboard 188 (FIG. 3) of the base station 154 (FIG. 3). The tablet computer 100 preferably is plugged into the base station 154 (FIG. 3) during transcription since the tablet computer 100 preferably does not have a keyboard. In an alternative embodiment (not shown), the tablet computer is provided with a keyboard jack into which a keyboard is plugged during the transcription process.

FIG. 18 shows the text window 408 with text 436 after the medical specialist has transcribed the voice annotation 410. The text window 408 preferably is programmed with a conventional word-processor, many of which are well known in the art, to permit the medical specialist to edit the text 436 in the text window 408. When a keyboard is used to enter the transcription, function keys on the keyboard should preferably be mapped to the audio playback controls to reduce hand movement back and forth between the keyboard and the display. The medical specialist preferably saves the transcribed text by tapping a save button 438.

Tapping a delete button 440 preferably deletes the voice data. The medical specialist preferably can delete the voice data after it has been transcribed in order to conserve memory. A confirm cycle preferably is provided in order to prevent the accidental deletion of voice data. In an alternative embodiment (not shown), the delete button 440 preferably is omitted in order to ensure that voice data is not accidentally deleted. This embodiment may be preferable when sufficient memory is available to store numerous voice annotations.

If the medical specialist wishes to transcribe a different voice annotation, he or she taps the desired voice annotation in the transcription menu 406 and then taps the transcribe button 418. Selecting a new voice annotation preferably causes the voice annotation currently displayed in the text window 408 to be saved and the newly selected voice annotation to appear in the text window 408. A confirm cycle can be provided before the previously displayed voice annotation is saved.

The medical specialist taps a done button 442 in order to exit the transcription display screen and return to the saved catalog menu (FIG. 15). Any voice annotation appearing in the text window 408 when the done button 442 is pressed preferably is automatically saved before returning to the saved catalog menu (FIG. 15). A confirm cycle can be provided before the displayed voice annotation is saved.

Referring back to FIG. 15, the physician or medical specialist exits the save catalog menu by tapping a close button 444. Tapping the close button 444 deletes all sets of saved data currently marked with "DEL".

Figure 19:
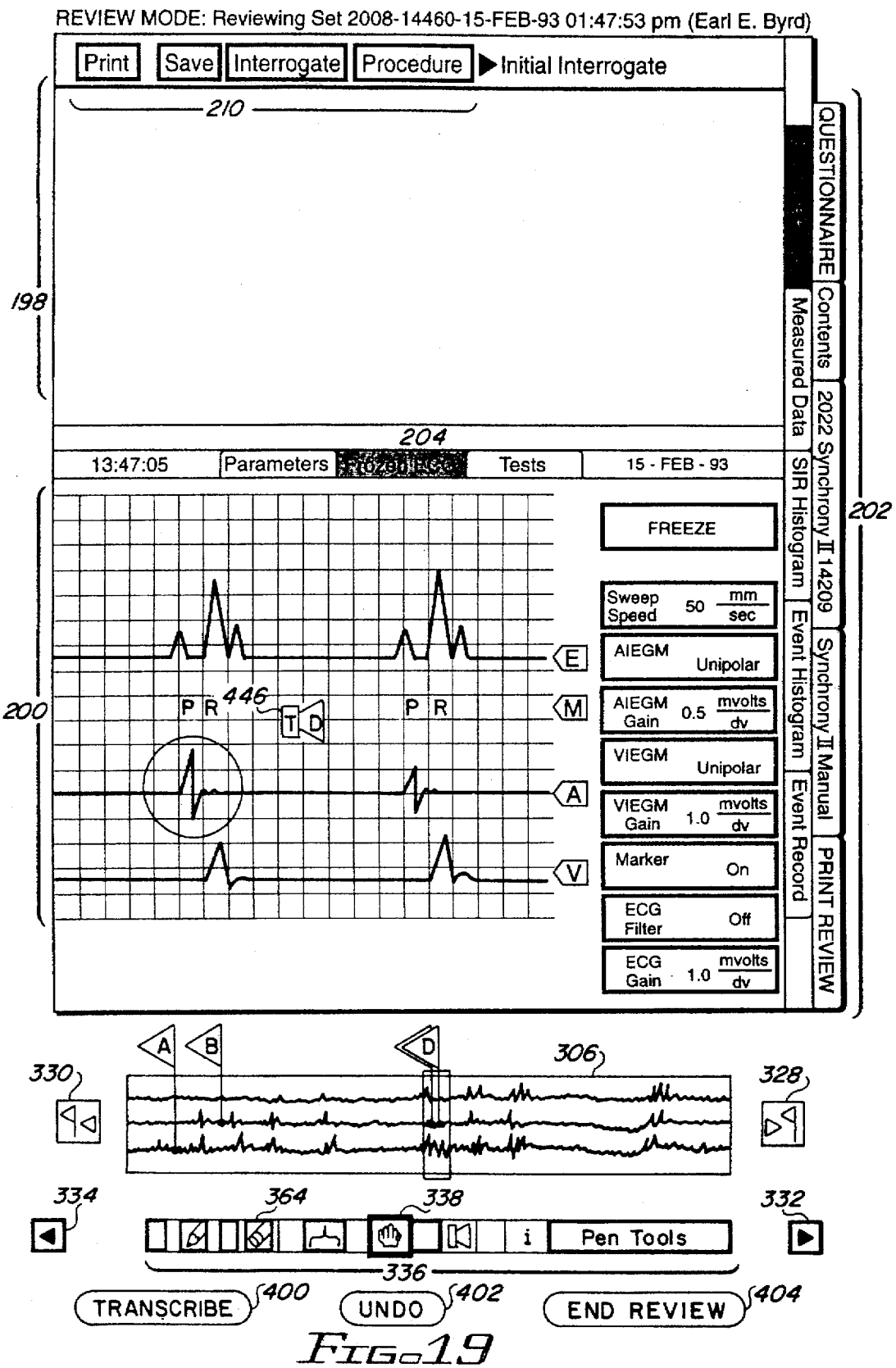
FIG. 19 is a preferred screen display in the review mode after a voice annotation has been transcribed.

FIG. 19 shows the display screen in the review mode after the voice annotation has been transcribed. A modified voice annotation marker 446 appears in the lower window 200. The letter "T" (in addition to the letter "D") preferably appears within the modified voice annotation marker 446 in order to indicate that the voice annotation has been transcribed.

Figure 20:
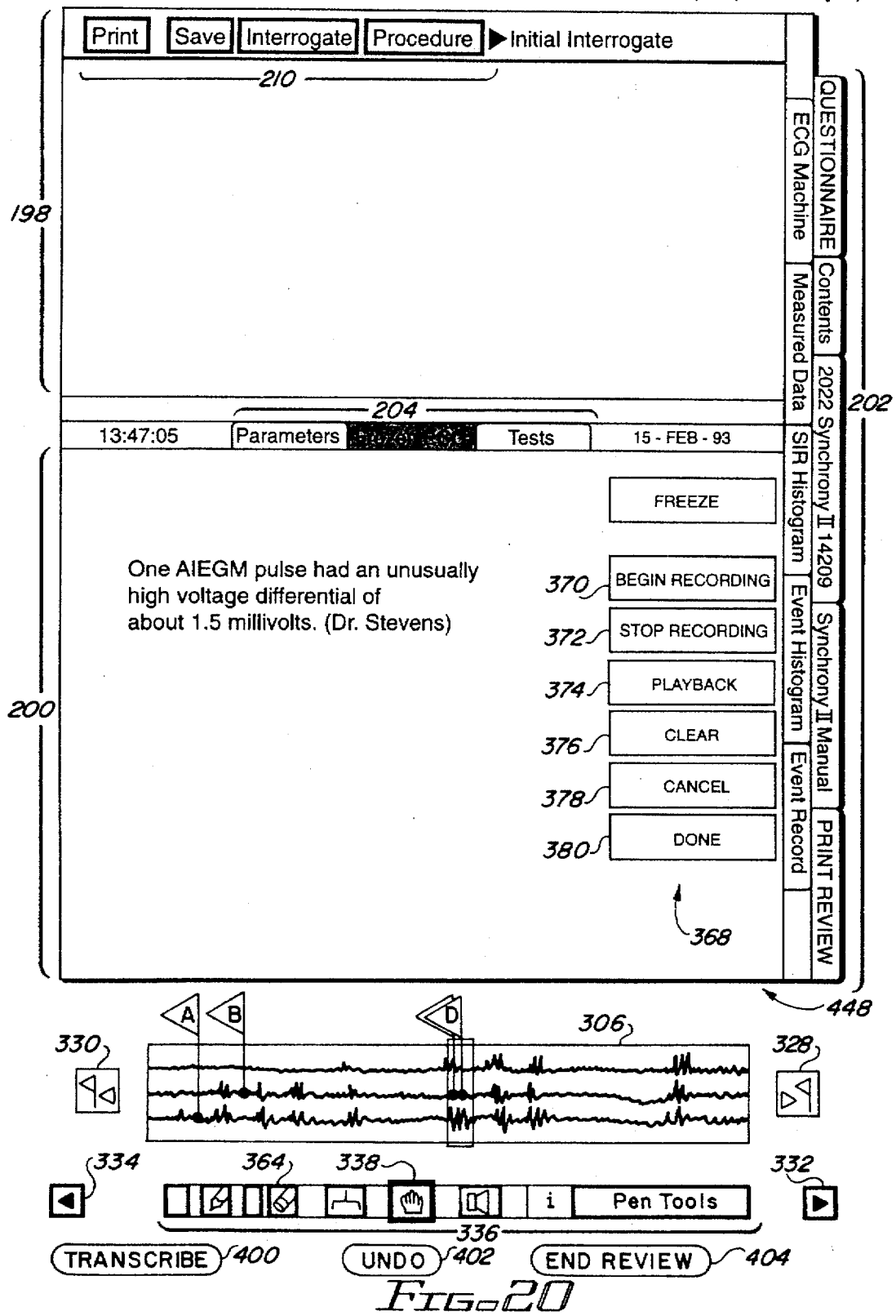
FIG. 20 is preferred screen display in the review mode after the voice annotation marker of FIG. 22 has been selected.

When the user selects the modified voice annotation marker 446, the text of the voice annotation preferably appears in a text window 448 as shown in FIG. 20. Once the voice annotation has been selected, the physician preferably can add further voice data to the voice annotation using the control window 368. In particular, tapping the begin recording button 370 permits the physician to record voice data which preferably is added to the end of the previous voice annotation, rather than replacing the previous voice annotation. (Of course, if the previous voice annotation was deleted after having been transcribed, then the newly recorded voice data will be the only voice data saved.) When the physician is finished recording the additional voice data, he or she taps the stop recording button 372.

Tapping the playback button 374 preferably causes the voice annotation to be played back, including any newly recorded voice data. If the previous voice annotation was deleted after having been transcribed, only the newly recorded voice data is played back.

Tapping the clear button 376 preferably deletes all voice data entered since the voice annotation was selected. That is, tapping the clear button 376 preferably does not effect any voice data recorded before the voice annotation marker 364 was selected for display. A confirm cycle preferably is provided when the clear button 376 is pressed in order to prevent the accidental deletion of voice data. As is the case when recording a new voice annotation, the control window 368 preferably remains displayed after the clear button 376 is pressed.

Tapping the cancel button 378 preferably ends the display of the transcribed voice annotation without saving the voice data recorded while the voice annotation marker 364 was selected. Previously recorded voice data preferably is not effected by tapping the cancel button 378. A confirm cycle preferably is provided when the cancel button 378 is pressed in order to prevent the accidental deletion of voice data.

Tapping the done button 380 preferably ends the display of the transcribed voice data and preferably saves any additional voice data that was recorded while the voice annotation marker 364 was selected.

In an alternative embodiment, during the transcription of a voice annotation, the display screens shown in FIGS. 15-18 preferably are displayed on the display screen 175 (FIG. 3) of the base computer 154 (FIG. 3), rather than on the display screen of the tablet computer 100. Using the display screen 175 (FIG. 3) of the base computer 154 (FIG. 3) may be more convenient than using the display screen of the tablet computer 100 because the keyboard 188 (FIG. 3) of the base computer 154 (FIG. 3) preferably is used to transcribe a voice annotation. In this embodiment, rather than using the digitizer pen 102 (FIG. 1) to select items on the display screen, the physician or medical specialist preferably uses a "mouse" or similar such input device (not shown) to select items on the display screen of the base computer 154 (FIG. 3). The use of such input devices to select items on a display screen is well known to those skilled in the art.

Another alternative embodiment of the present invention is shown in FIG. 21. In this embodiment, the transcription of voice data is carried out using the digitizer pen 102 (FIG. 1) rather than using a keyboard. The elements displayed on the display screen in this embodiment preferably are the same as those shown in FIGS. 17 and 18, and are thus labeled with the same reference numbers (except for the ink tool icon 450, text window 452, and text 454 as explained below). The like-numbered elements operate in the same manner as those described above in reference to FIGS. 17 and 18 and will not be discussed further here. After selecting the voice annotation 410 for transcription, the medical specialist taps an ink tool icon 450 to allow the pen 102 (FIG. 1) to write in the text window 452. When the medical specialist is finished writing he or she taps the ink tool icon 450 again. The medical specialist saves handwritten text 454 by tapping the save button 438. In this embodiment, the display screen shown in FIG. 21 is displayed on the display screen of the tablet computer 100 so that the user can write with the digitizer pen 102 (FIG. 1).

Figure 22:
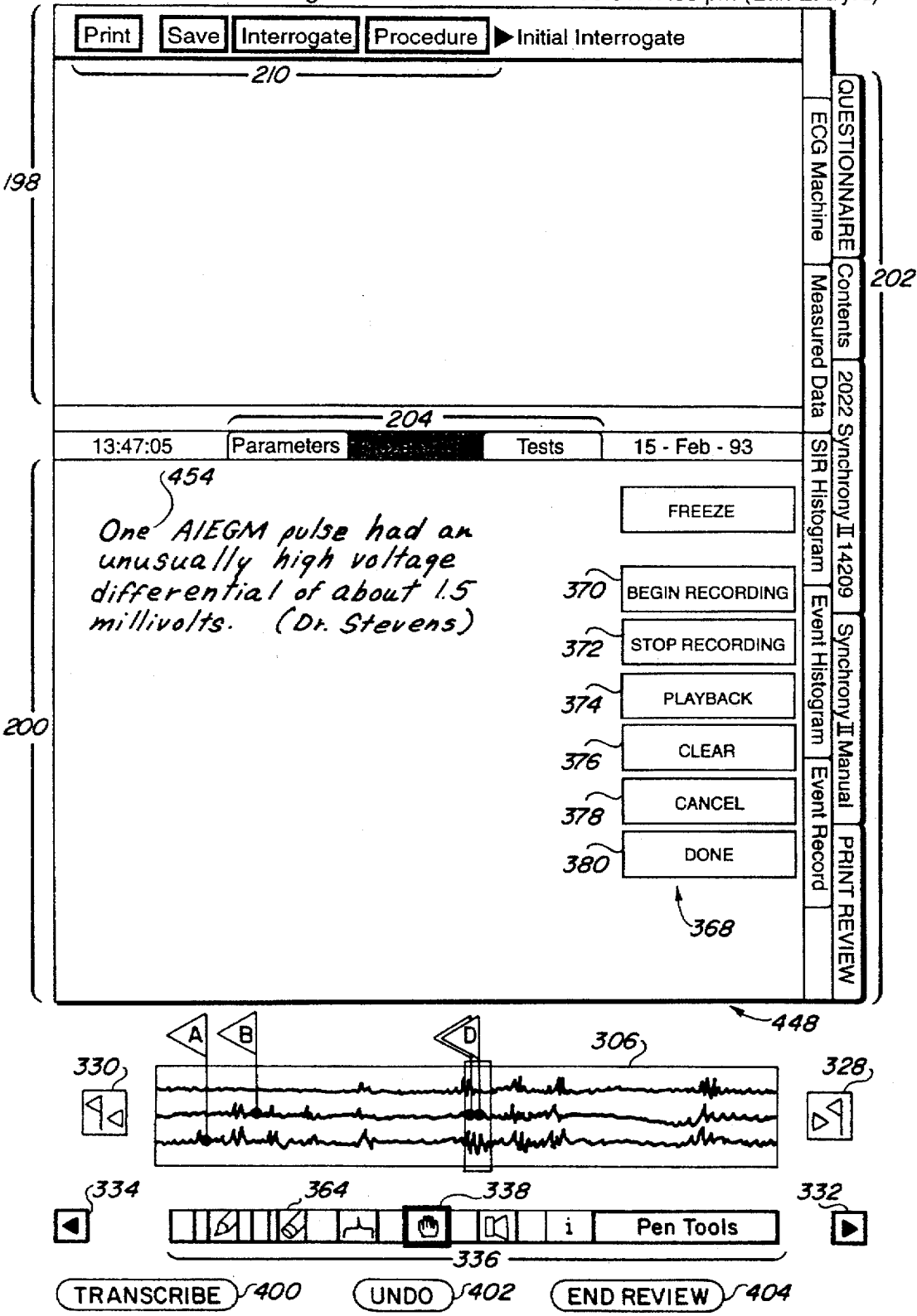
FIG. 22 is an alternative screen display in the review mode showing a voice annotation that has been transcribed using a digitizer pen.

FIG. 22 shows the display of the transcribed voice annotation in the review mode (i.e., similar to the display screen shown FIG. 20). In this embodiment, the text window 488 displays the handwritten text 454 in the lower display window 200.

Figure 23:
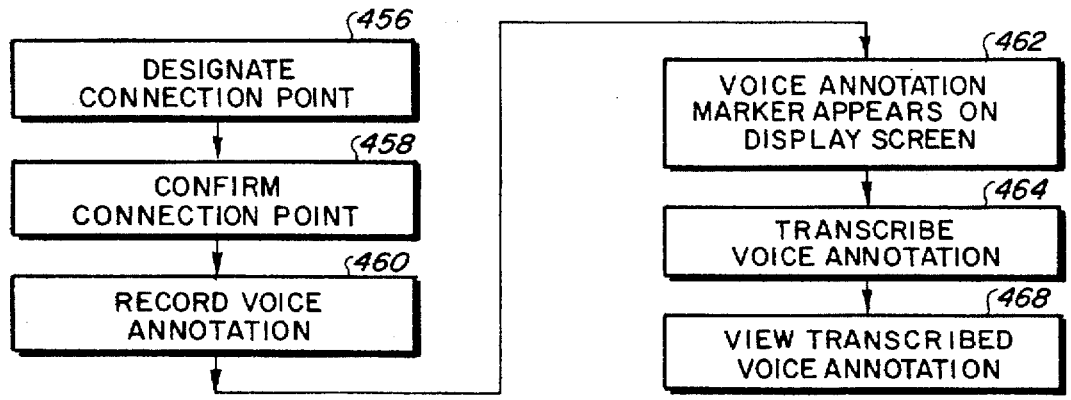
FIG. 23 is a sequence of steps for carrying out a preferred embodiment of the present invention.

FIG. 23 shows an illustrative sequence of steps for recording and transcribing a voice annotation in accordance with the present invention. These steps have already been described in detail, and so the following discussion simply summarizes the detailed processing steps provided above. At step 456 the user designates a connection point of the patient data scroll. At step 458 the user is asked to confirm the connection point designated at step 456. (Step 458 can be omitted, especially in the case of experienced users.) At step 460 the user records the voice annotation. At step 462 a voice annotation marker appears on the display screen of the tablet computer 100 (FIG. 1) at a location corresponding to the connection point designated at step 456. At step 464, an appropriate medical specialist transcribes the voice annotation. At step 468 the text of the transcribed voice annotation is displayed on the display screen of the tablet computer 100 (FIG. 1).

The print options preferably available when using tablet computer 100 are described in detail in the aforementioned '367 application and will not be discussed further here. Voice annotations are not printed, of course, because they comprise sounds rather than printed matter. However, once a voice annotation is transcribed, the transcribed annotation can be printed in a manner substantially similar to the manner in which ink annotations are printed as described in the aforementioned '367 applicatation.

Thus, methods and apparatus for annotating data in an implantable device programmer using digitally recorded sound have been provided. One skilled in the art will appreciate that the present invention can be practiced by other than the described embodiments, which are presented for purposes of illustration and not of limitation, and the present invention is limited only by the claims which follow.

What is claimed is:

1. An implantable device programmer comprising:

processing means;

memory means coupled to said processing means for storing digital data;

display means coupled to said processing means for displaying a graphical representation of at least a part of a patient data set;

transducing means for converting audio signals into electrical signals; and analog to digital converter means coupled to said processing means and said transducing means for converting said electrical signals into digital voice data, wherein said processing means causes said digital voice data to be stored in said memory means and linked to a portion of said patient data set.

2. The apparatus of claim 1, further comprising input means coupled to said processor means for designating said portion of said patient data set to which said digital voice data are linked.

3. The apparatus of claim 2, wherein a connection point is designated using said input means in order to designate said portion of said patient data set to which said digital voice data are linked.

4. The apparatus of claim 3, wherein said processing means causes a voice annotation marker to be displayed on said display means at a location corresponding to said connection point.

5. The apparatus of claim 2, further comprising speaker means coupled to said processor means for playing back said digital voice data.

6. The apparatus of claim 5, wherein said processing means causes a playback indicator to be displayed on said display means and causes said digital voice data to be played back via said speaker means when said playback indicator is selected using said input means.

7. The apparatus of claim 2, wherein said input means comprises a digitizer pen and said display means comprises a digitizer display screen for transcribing said digital voice data by writing on said digitizer display screen so as to provide transcribed digital voice data which said processing means causes to be stored in said memory means.

8. The apparatus of claim 2, further comprising keyboard means coupled to said processor means for transcribing said digital voice data so as to provide transcribed digital voice data which said processing means causes to be stored in said memory means.

9. The apparatus of claim 8, wherein said processing means causes said transcribed digital voice data to be linked to said portion of said patient data set.

10. The apparatus of claim 9, wherein said processing means causes a voice annotation marker which indicates that said digital voice data have been transcribed to be displayed on said display means at a location corresponding to said portion of said patient data to which said digital voice data are linked.

11. The apparatus of claim 10, wherein said processing means causes said transcribed digital voice data to be displayed on said display means when said voice annotation marker is selected using said input means.

12. The apparatus of claim 2, wherein said input means comprises a digitizer pen.

13. An analyzer-programmer for use with an implantable cardiac stimulating device implanted within a patient, said analyzer-programmer comprising:

processing means;

telemetry means coupled to said processing means for receiving information from and transmitting information to said implantable cardiac stimulating device;

memory means coupled to said processing means for storing digital data;

display means coupled to said processing means for displaying a graphical representation of at least a portion of a patient data set comprising information relating to the patient's condition received via said telemetry means;

input means for designating a connection point of said patient data set;

transducing means for converting audio signals into electrical signals; and analog to digital converter means coupled to said processing means and said transducing means for converting said electrical signals into digital voice data, wherein processing means causes said digital voice data to be stored in said memory means and linked to said connection point of said patient data set.

14. The apparatus of claim 13, wherein said information relating to the patient's condition includes at least one of an atrial IEGM, a ventricular IEGM and marker data.

15. The apparatus of claim 13, wherein said processing means causes a voice annotation marker to be displayed on said display means at a location corresponding to said connection point.

16. The apparatus of claim 15, further comprising speaker means coupled to said processor means, wherein said processing means causes a playback indicator to be displayed on said display means and causes said digital voice data to be played back via said speaker means when said playback indicator is selected using said input means.

17. The apparatus of claim 16, further comprising keyboard means coupled to said processor means for transcribing said digital voice data so as to provide transcribed digital voice data which is stored in said memory means.

18. The apparatus of claim 17, wherein said processing means causes a voice annotation marker indicating that said digital voice data have been transcribed to be displayed on said display means at a location corresponding to said portion of said patient data to which said digital voice data are linked.

19. The apparatus of claim 18, wherein said processing means causes said transcribed digital voice data to be displayed on said display means when said voice annotation marker is selected using said input means.

20. A method of operating an implantable device programmer comprising the steps of:

displaying on display means a graphical representation of at least a part of a patient data set;

receiving audio signals via transducer means;

converting said audio signals into electrical signals using said transducer means;

converting said electrical signals into digital voice data using analog to digital converter means;

storing said digital voice data in memory means; and linking said digital voice data to a portion of said patient data set.

21. The method of claim 20, wherein the step of linking said digital voice data to a portion of said patient data set comprises designating said portion of said patient data set using input means.

22. The method of claim 21, further comprising the step of displaying a voice annotation marker on said display means at a location corresponding to said portion of said patient data set.

23. The method of claim 22, further comprising the step of playing back said digital voice data using speaker means.

24. The method of claim 23, further comprising the step of displaying a playback indicator on said display means, and wherein the step of playing back said digital voice data using said speaker means comprises playing back said digital voice data using said speaker means when said playback indicator is selected using said input means.

25. The method of claim 21, wherein said input means comprises a digitizer pen and wherein said display means comprises a digitizer display screen, the method further comprising the steps of:

transcribing said digital voice data by writing on said digitizer display screen with said digitizer pen so as to provide transcribed digital voice data; and storing said transcribed digital voice data in said memory means.

26. The method of claim 21, further comprising the steps of:

transcribing said digital voice data using keyboard means so as to provide transcribed digital voice data; and storing said transcribed digital voice data in said memory means.

27. The method of claim 26, further comprising the step of displaying a voice annotation marker which indicates that said digital voice data have been transcribed on said display means at a location corresponding to said portion of said patient data set.

28. The method of claim 27, further comprising the step of displaying said transcribed digital voice data on said display means when said voice annotation marker is selected using said input means.

29. A method of operating an analyzer-programmer for use with an implantable cardiac stimulating device implanted within a patient, the method comprising the steps of:

receiving information relating to the patient's condition via telemetry means;

displaying on display means a graphical representation of at least a portion of a patient data set comprising said information relating to the patient's condition;

designating a connection point of said patient data set using input means;

receiving audio signals via transducer means;

converting said audio signals into electrical signals using said transducer means;

converting said electrical signals into digital voice data using analog to digital converter means;

storing said digital voice data in memory means; and linking said digital voice data to said connection point.

30. The method of claim 29, wherein the step of receiving information relating to the patient's condition comprises receiving at least one of an atrial IEGM, a ventricular IEGM and marker data, and said displaying step comprises displaying on said display means at least one of said atrial IEGM, said ventricular IEGM and said marker data.

31. The method of claim 30, further comprising the step of displaying a voice annotation marker indicating that said digital voice data have been transcribed on said display means at a location corresponding to said connection point.

32. The method of claim 31, further comprising the steps of:

displaying a playback indicator on said display means; and playing back said digital voice data using speaker means when said playback indicator is selected using said input means.

* * * * *